US010287332B2

(12) United States Patent
Cox et al.

(10) Patent No.: US 10,287,332 B2
(45) Date of Patent: May 14, 2019

(54) SELF-ASSEMBLED BETA SOLENOID PROTEIN SCAFFOLDS

(71) Applicant: The Regents of the University of California, Oakland, CA (US)

(72) Inventors: Daniel Cox, Oakland, CA (US); Gang-Yu Liu, Oakland, CA (US); Michael Toney, Oakland, CA (US); Xi Chen, Oakland, CA (US); Josh Hihath, Oakland, CA (US); Gergely Zimanyi, Oakland, CA (US); Natha Robert Hayre, Oakland, CA (US); Maria Peralta, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 182 days.

(21) Appl. No.: 15/111,687

(22) PCT Filed: Jan. 26, 2015

(86) PCT No.: PCT/US2015/012934
§ 371 (c)(1),
(2) Date: Jul. 14, 2016

(87) PCT Pub. No.: WO2015/112990
PCT Pub. Date: Jul. 30, 2015

(65) Prior Publication Data

US 2017/0058007 A1 Mar. 2, 2017

Related U.S. Application Data

(60) Provisional application No. 61/931,485, filed on Jan. 24, 2014.

(51) Int. Cl.

| | |
|---|---|
| ***C07K 14/47*** | (2006.01) |
| ***C07K 14/415*** | (2006.01) |
| ***C07K 14/435*** | (2006.01) |

(52) U.S. Cl.
CPC ...... *C07K 14/43563* (2013.01); *C07K 14/415* (2013.01); *C07K 14/47* (2013.01)

(58) Field of Classification Search
None
See application file for complete search history.

(56) References Cited

U.S. PATENT DOCUMENTS

2012/0063276 A1 3/2012 Reches et al.

OTHER PUBLICATIONS

Kajava and Steven, "The turn of the screw: Variations of the abundant beta-solenoid motif in passenger domains of Type V secretory proteins", Journal of Structural Biology 155: 306-315 (2006). (Year: 2006).*

Sakai et al., "Formation of Functionalized Nanowires by Control of Self-Assembly Using Multiple Modified Amyloid Peptides", Adv. Funct. Mater. 23: 4881-4887 (2013) (Year: 2013).*

Graether, et al. "Structural characterization of amyloidotic anti-freeze protein fibrils and intermediates." Journal of Toxicology and Environmental Health, Part A 72, No. 17-18 (2009): 1030-1033.

Scheibel, et al. "Conducting nanowires built by controlled self-assembly of amyloid fibers and selective metal deposition." Proceedings of the National Academy of Sciences 100, No. 8 (2003): 4527-4532.

Wasmer et al., "Amyloid Fibrils of the HET-s (218-289) Prion from a β Solenoid with a Triangular Hydrophobic Core," Science, vol. 319, No. 5869, (2008) pp. 1523-1526.

International Search Report dated Apr. 24, 2015 issued in PCT/US2015/012934.

Kajava et al., "β Arcades: recurring Motifs in Naturally Occurring and Disease-Related Amyloid Fibrils," The FASEB Journal, vol. 24, No. 5, May 2010 pp. 1311-1319.

Knowles et al., "Nanomechanics of Functional and Pathological Amyloid Materials," Nature nanotechnology, vol. 6, No. 8, (2011), pp. 469-479.

Peralta, et al., "Engineering Amyloid Fibrils from β-Solenoid Proteins for Biomaterials Applications," ACS Nano, vol. 9, No. 1, Jan. 6, 2015, pp. 449-463.

Sakai et al., "Formation of Functionalized Nanowires by Control of Self-Assembly Using Multiple Modified Amyloid Peptides," Adv. Funct. Mater. vol. 23, No. 39, 2013, pp. 4881-4887.

* cited by examiner

*Primary Examiner* — Anand U Desai
(74) *Attorney, Agent, or Firm* — Kilpatrick Townsend & Stockton LLP

(57) ABSTRACT

The present invention provides amyloid fibrils comprising a plurality of modified β solenoid protein (mBSP) monomers. The mBSP monomers are modified to enhance self-assembly and are useful in a variety of applications.

7 Claims, 12 Drawing Sheets

Specification includes a Sequence Listing.

SELF-ASSEMBLED BETA SOLENOID PROTEIN SCAFFOLDS

CROSS-REFERENCES TO RELATED APPLICATIONS

This application is a 371 U.S. National Phase Application of PCT/US2015/012934, filed Jan. 26, 2015 which claims benefit under 35 U.S.C. § 119(e) to U.S. Application No. 61/931,485, filed Jan. 24, 2014 the contents of which are incorporated herein by reference.

STATEMENT AS TO RIGHTS TO INVENTIONS MADE UNDER FEDERALLY SPONSORED RESEARCH AND DEVELOPMENT

This work was supported by grants from the National Science Foundation (DMR-1207624 and DMR-0844115). The US Government may have certain rights in this invention.

REFERENCE TO SUBMISSION OF A SEQUENCE LISTING AS A TEXT FILE

The Sequence Listing written in file SEQ-1016884.txt created on Nov. 3, 2016, 22.1 bytes, machine format IBM-PC, MS-Windows operating system, is hereby incorporated by reference in its entirety for all purposes.

FIELD OF THE INVENTION

The present invention relates to amyloid fibers prepared from modified β solenoid protein monomers. The monomers are used for binding nanoparticles and other functional entities in a variety of applications.

BACKGROUND OF THE INVENTION

An important goal of nanotechnology is bottom-up manufacturing of useful devices and materials via self-assembly at room temperature in environmentally benign solvents. Living systems provide numerous examples of such self-assembly in the guise, for example, of protein structures such as microtubules,[1] viral capsids,[2] bacterial s-layers,[3] and amyloid fibrils[4] in which proteins grow in one-dimensional filaments with β-strands perpendicular to the growth axis.

The programmable design of DNA-based nanostructured scaffolds is extraordinary,[5] allowing for the templating of ordered heterogeneous arrays of, e.g., metallic nanoparticles,[6] proteins,[7] and semiconducting wires.[8] However, it is plagued with technical barriers to advancement, including: a) difficulties in scaling it to industrial applications, b) high error rates of DNA replication, c) denaturation of DNA scaffolds/bundles at moderate temperatures (~60° C.), and d) loss of integrity under exposure to ultraviolet light and enzymes,[9] e) very limited capability to carry a broad range of functional groups; f) limited tenability in terms of ternary and quaternary structures.

Belcher and collaborators have used the M13 virus as a scaffold for self-assembly of a wide variety of inorganic materials. Their strategy relies on modifying coat proteins with peptides that are selected through phage display for templating a specific material.[10] In one example, the M13 major coat protein was coated by a peptide with $FePO_4$-nanoparticle templating activity while the attachment proteins at the end of the virus were fused to a peptide known to adhere to carbon nanotubes.[11] Incubation of the virus with iron and phosphate ions together with single-walled carbon nanotubes generated a self-assembled working cathode. However, the M13 approach is limited by several factors: (a) viruses are large (M13 is nearly a micron in length); (b) templating sites are limited to the coat proteins, and the geometry is restricted to that provided by the virus; (c) while the viruses can order as liquid crystals, the ordering is on the micron scale; and (d) the capability to engineer or program designed structure is difficult as the product is at the mercy of viral scaffold. Hence, precise, programmable nanometer-scale ordered heterogeneity, as achieved with DNA, is not feasible.

Amyloid fibrils are self-assembled one-dimensional protein arrays with fi-strands perpendicular to the linear axis.[4] They arise both in unregulated self-assembly in numerous diseases including Alzheimer's disease and type II diabetes, as well as in regulated contexts in biofilm extracellular matrices,[12] synapse formation,[13] and hormone reservoir manufacture.[14] These fibrils have bending and twisting persistence lengths on the micron scale,[15, 16] which contribute to the remarkable tensile strength of spider silk[17] and the structural stability of barnacle cement.[18] They have previously been used to template metallic nanowire growth,[19-21] and have been used to produce mechanically strong oriented films.[22]

Amyloid structures are remarkably robust. Generally, they can survive heating to the boiling point of water[23-25] although there is monomer size and sequence dependence to this result. They are resistant to protease degradation[26, 27] and UV light exposure. To date, amyloids have not been assembled to produce a significant level of transverse order, nor have they been used to template material growth other than the examples given above. There is also little systematic understanding of amyloid structure because the lack of transverse order makes it difficult for X-ray diffraction to reveal more than the generic cross β-stacking,[28] although in some instances additional scattering rings in fiber diffraction have provided information about transverse dimensions of fibrils and longer periodicity repeats along the fiber axis.[29]

BRIEF SUMMARY OF THE INVENTION

The present invention provides amyloid fibrils comprising a plurality of modified β solenoid protein (mBSP) monomers. The monomers may be derived from a variety of sources, such as antifreeze proteins. The mBSP monomers are modified to enhance self-assembly, by for example, removing an end cap that prevents amyloid aggregation. The mBSPs may also be modified to include at least one amino acid residue that promotes attachment of the fibril to a solid support, a nanoparticle, a biological molecule (e.g., an enzyme), a bacterial or eukaryotic cell (in which case the scaffold can be used a matrix for tissue growth), or additional amyloid fibrils.

The invention also provides method of forming a nanomaterial. The methods comprise (a) contacting a plurality of nanoparticles with a scaffold comprising at least one amyloid fibril comprising a plurality of modified β solenoid protein (mBSP) monomers; and (b) fusing the nanoparticles to form the nanomaterial. The methods may further comprise the step of attaching the scaffold to a solid support prior to the step of contacting the plurality of nanoparticles with the mBSP scaffold. The nature of the nanoparticles is not critical to the invention and can be selected based on the desired function to be achieved.

The invention further provides scaffolds comprising at least one amyloid fibril of the invention. The scaffold is typically bound to a plurality of nanoparticles.

Definitions

The term "β-solenoid protein" (BSP) refers to proteins having backbones that turn helically in either a left- or right-handed sense around the long axis of the protein from the N-terminus to the C-terminus to form β-sheets, and have regular geometric structures (triangles, rectangles, etc.) with 1.5-2 nm sides. The wild type (WT) BSPs are inhibited from amyloid aggregation (end-to-end polymerization to give cross β-fibrils) by natural capping features and/or structural irregularities on one or both ends. Examples of non-amyloidogenic WT-BSPs that can form amyloid fibrils upon modification include, one-sided antifreeze proteins (*Tenebrio molitor* AFP-Protein Database (PDB) Accession No. 1EZG), two-sided antifreeze (Snow Flea AFP-PDB 2PNE and 3BOI), rye grass AFP (PDB-3ULT), three-sided "type II" left handed β-helical solenoid antifreeze proteins, for example from the spruce budworm (PDB 1M8N), three-sided bacterial enzymes (PDB 1LXA, 1FWY, 1G95, 1HV9, 1J2Z, 1T3D, 1THJ, 1KGQ, 1IMR7, 1SSM, 2WLC, 3R3R, 1KRV, 3EH0, 3Q1X, 3BXY, 3HJJ, 3OGZ, 4M98, 4IHH (acyltransferases, γ-class carbonic anhydrases and homologs), three-sided motor proteins subunits (e.g., PDB 3TV0), a three-sided "type I" left handed β-helical enzyme ydcK from *Salmonellae cholera* (2PIG), four-sided proteins (PDB 2BM6, 2W7Z, 2J8I), four-sided pentapeptide repeat proteins (2G0Y and 3DU1), and 1XAT. One of skill will recognize that the full sequence of each of these proteins is available from the Protein Database.

The term "modified β solenoid protein (mBSP)" (also referred to as mBSP monomers) refers to genetically engineered β solenoid proteins that allow for controlled amyloid self-assembly. One of skill will recognize that an mBSP monomer can be engineered to be any desired length and can tailored to the particular application. In a typically embodiment, the monomer will comprise at least two beta sheet rungs (about 30-36 residues) and more often at least three rungs (about 45-54 residues). The typical size of a beta strand face is about 3-6 residues, including bends the edge size will usually not exceed 5-8 residues, which is a range of about 2-3.2 nm. One of skill will recognize that a number of modifications can be used to allow for self-assembly. For example, many BSPs include end caps that can be removed to allow for controlled amyloid self-assembly. Similarly, many BSPs include disulfides, bulges, and prolines that require removal to allow for controlled amyloid self-assembly. One of skill will recognize that the three dimensional structure of any given BSP can be used to design an mBSP of that desired shape. Means for modeling engineered proteins and characterizing their final properties are well known to those of skill. Exemplary techniques for these procedures are described in detail below. Examples of mBSPs include SBAFP-m1 (SBAFP with endcap and disulfides removed), and RGAFP-m1 (RGAFP with bulges and proline removed), both of which are described in more detail below.

The mBSPs of the invention can be functionalized in designed ways to specifically carry designated functional units. This includes substitution of amino acid residues with side chains having desired reactivity. In some embodiments, these residues are at the end of a nanoparticle binding peptide, linked to the mBSP monomer. The residues can be selected to allow attachment of the mBSP or fibril to a solid support, a nanoparticle, a biological molecule (e.g., an enzyme), a bacterial or eukaryotic cell (in which case the scaffold can be used a matrix for tissue growth), or additional amyloid fibrils. For example, the mBSP monomers can be modified to include residues that enhance hydrophobic interactions and/or salt bridging. Peptide bond chemistry, threonine bonding, disulfide bridges, or metal mediated chelation of histidine side chains can also be used. One of skill will recognize that by adjusting the side chain structures on different faces of mBSPs, programmable lateral assembly that can allow specific geometric arrangement of the BSP scaffold can be achieved. Modifications of external side chains of the mBSPs can be used to enable binding to nanoparticles, nanoparticle templating molecules, solid supports, or for specific lateral self-assembly in two or three dimensions. One of skill will recognize a number of modifications that can be used to enable such binding.

The term "amyloid fibril" refers to fibrous protein aggregates that polymerize end-to-end in one-dimensional protein arrays. Amyloid fibrils can form naturally or they can be produced out of intrinsically non-amyloidogenic proteins. As shown here, using a rational design concept, intrinsically non-amyloidogenic proteins (e.g., BSPs) with natural cross-β structure can be transformed into proteins that readily self-assemble into amyloid fibrils under benign conditions.

The term "mBSP scaffold" refers to a system of one or more amyloid fibrils comprising mBSP monomers, that can be a platform for biomaterial-based self-assembly.

The term "antifreeze protein or AFP" refers to a protein found in the body fluids of some poikilothermic organisms, such as, *Choristoneura* sp. *C. fumiferana* or *C. occidentalis*, the *Tenebrio molitor* mealworm and plants which have the commonly known property that they reduce non-colligatively the freezing point of water. As used herein, "antifreeze proteins" are chemically synthesized or recombinantly produced polypeptides having a protein sequence with substantial similarity to a naturally occurring antifreeze protein and retaining the properties of an antifreeze polypeptide. In some embodiments, the modified antifreeze proteins of the invention will have altered or improved antifreeze activity and can be used for that purpose, as well.

Those of skill recognize that many antifreeze protein are BSPs. For example, those derived from *Tenebrio*, Snow Flea rye grass, and the spruce budworm. Other examples of antifreeze proteins useful in the present invention include those described in the following PDB Accessions: 3VN3_B, 3VN3_A, 4DT5_B, and 4DT5_A.

The term "nanoparticle" refers to a microscopic particle with at least one dimension less than 100 nm. Examples of nanoparticles include nanomaterial precursors, inorganic nanoparticles, and catalysts. The nanoparticle can also be conjugated to a biomolecule (e.g., DNA, RNA, or a protein, such as an enzyme). The nanomaterial precursors can include inorganic materials that form nanomaterials such as inorganic nanocrystals. The nanoparticle can also possess optimal metal binding capabilities including the ability to bind cadmium, iron, nickel, radium, uranium, cobalt, lead, manganese or arsenic. The nanomaterial of the invention can comprise or consist essentially of materials such as, for example, semiconducting materials, whether doped or undoped; metallic materials; metal oxide materials, and magnetic materials. Various oxide materials including silica and alumina can also be used. Nanoparticles can include a metal oxide compound. The metal oxide can include a manganese oxide, a magnesium oxide, an aluminum oxide, a silicon oxide, a zinc oxide, a copper oxide, a nickel oxide, a cobalt oxide, an iron oxide, a titanium oxide, yttrium oxide, a zirconium oxide, a niobium oxide, a ruthenium oxide, a rhodium oxide, a palladium oxide, a silver oxide, an indium oxide, a tin oxide, an lanthanum oxide, an iridium oxide, a platinum oxide, a gold oxide, a cerium oxide, a neodymium oxide, a praseodymium oxide, an erbium oxide, a dysprosium oxide, a terbium oxide, a samarium oxide, a lutetium oxide, a gadolinium oxide, a ytterbium oxide, a europium oxide, a holmium oxide, a scandium oxide, uranium, uranium compounds, thorium or a combination thereof. As discussed below, from these inorganic nanoparticles, a inorganic nanomaterial of the invention can be formed consisting essentially of the fused inorganic nanoparticles upon substantial removal of the scaffold.

The terms "identical" or percent "identity," in the context of two or more nucleic acids or polypeptide sequences, (e.g., two mBSPs of the invention and polynucleotides that encode them) refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides of the invention, refers to two or more sequences or subsequences that have at least 60%, 65%, 70%, 75%, 80%, or 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (on world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides of the invention are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

DETAILED DESCRIPTION

Figure 1:
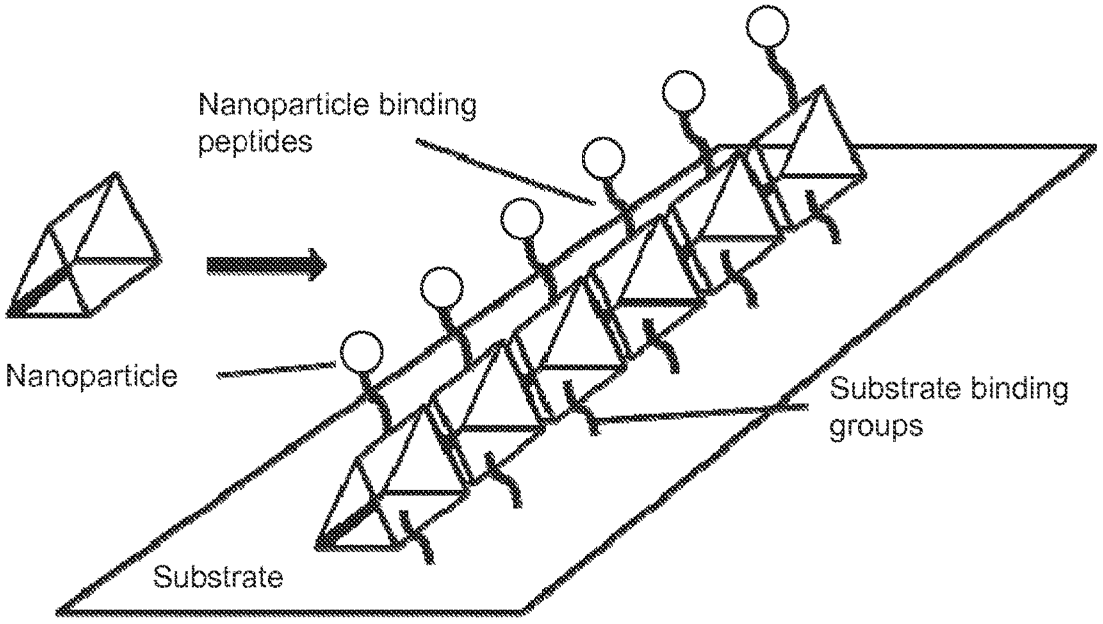
FIG. 1 is a schematic drawing of a amyloid fibril scaffold of the invention. The scaffold comprises a series of mBSP monomers bound to a solid support and each linked to a nanoparticle through a nanoparticle binding peptide.
Figure 2:
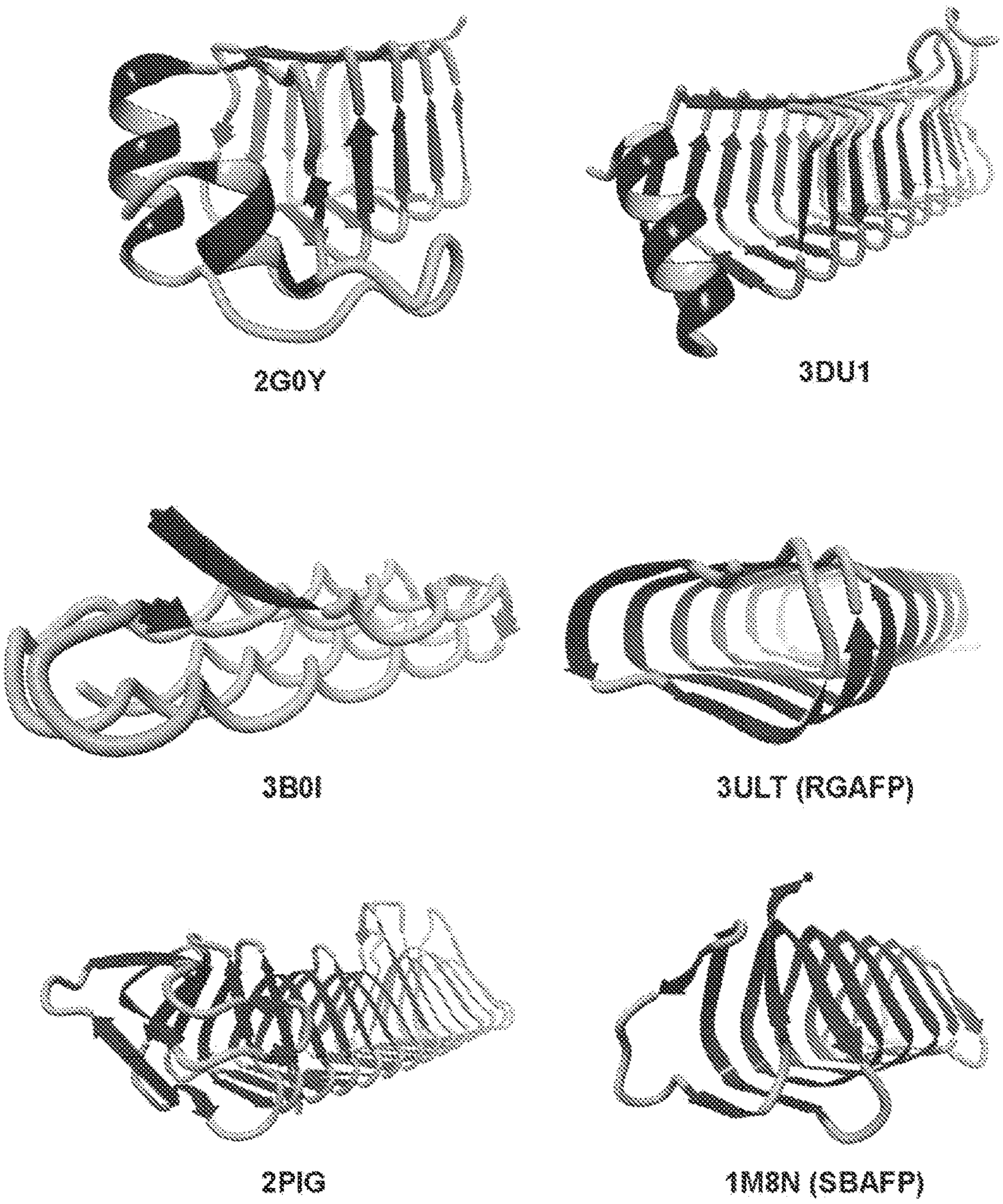
FIG. 2 shows examples of wild type β-solenoid proteins. PDB IDs are given below each. 2G0Y[68] and 3DU1[69] are four-sided pentapeptide repeat proteins. 3B0I[70] is a two-sided snow flea antifreeze protein. 3ULT[71] is the two-sided rye grass antifreeze protein abbreviated RGAFP herein. 2PIG[72] is the three-sided "type I" left handed β-helical enzyme ydcK from *Salmonellae cholera.* 1M8N[73] is the three-sided "type II" left handed β-helical solenoid anti-freeze protein from the spruce budworm abbreviated SBAFP herein.

The present invention provides a new approach to amyloid design that allows programmable nanoscale structural precision for self-assembly of materials under mild conditions. The invention uses naturally occurring β-solenoid proteins (BSPs). These proteins have backbones that turn helically in either a left- or right-handed sense from the N-terminus to form β-sheets, and have regular geometric structures (triangles, rectangles, etc.) with 1.5-2 nm sides. The WT proteins are inhibited from amyloid aggregation (end-to-end polymerization to give cross β-fibrils) by natural capping features and/or structural distortions on one or both ends. The present invention describes the modifications necessary to make linear polymers (amyloids) from these proteins, molecular simulations used to assess structural stability and geometric properties for comparison to measurements, and the protocol for expressing and folding of the engineered proteins. As shown here, the correct monomeric structures can be obtained after purification and folding, amyloid fibrils can be produced by incubation at elevated temperatures, and the kinetics of fibril formation are consistent with, though slightly faster than, other amyloid polymerization reactions. These conclusions are supported by measurements of circular dichroism (CD), thioflavin-T (ThT) fluorescence, dynamic light scattering (DLS), turbidity, and atomic force microscopy (AFM).

Modified Beta Solenoid Proteins

The modified BSPs of the invention offer excellent platforms for functionalization in nanotechnology without interfering with the native β-sheet structure. For example, the large area faces together with their designable length can, in principle, support nanoparticle binding peptides of more than one kind of nanoparticle to grow ordered heterogeneous nanoparticle arrays. Additionally, staggered placement of identical nanoparticle binding peptides can be used to control nanoparticle aspect ratio. Even as one face is being used for nanoparticle templating, another can be used for binding to surface or assuring designed lateral assembly of the fibrils. In contrast, strategies based upon small amyloidogenic peptides do not immediately offer this level of functionalization diversity.

In a typical embodiment, the mBSP is modified to enable one-dimensional growth through cross-beta strand (amyloid) pairing mBSPs. The exteriors and interiors of the proteins can also be modified to enable more efficient production. Usually, the protein units are allowed to self-assemble in one dimension after expressing proteins in *E. coli*, followed by subsequent cell lysis, purification, denaturation, and aggregation of the proteins to create the one dimensional scaffolds.

In some embodiments, at least two different mBSP monomers are designed to self-assemble in a predetermined order. This can be achieved by modifying the ends of the monomers such that, for example, the N-terminus of a first monomer interfaces with the C-terminus of a second monomer, but not with the C-terminus of another copy of the first monomer. The resulting fibril comprises the two different monomers in predetermined order (e.g., A-B-A-B-A-B, or A-B-C-A-B-C).

The correct molecular mass of the amyloid fibril can be verified through standard techniques, such as mass spectroscopy. The correct beta content can be determined through techniques such as circular dichroism. Amyloid aggregation can be confirmed by observing the growth of thioflavin T (ThT) fluorescence at 480 nm, according to standard techniques.

Figure 8:
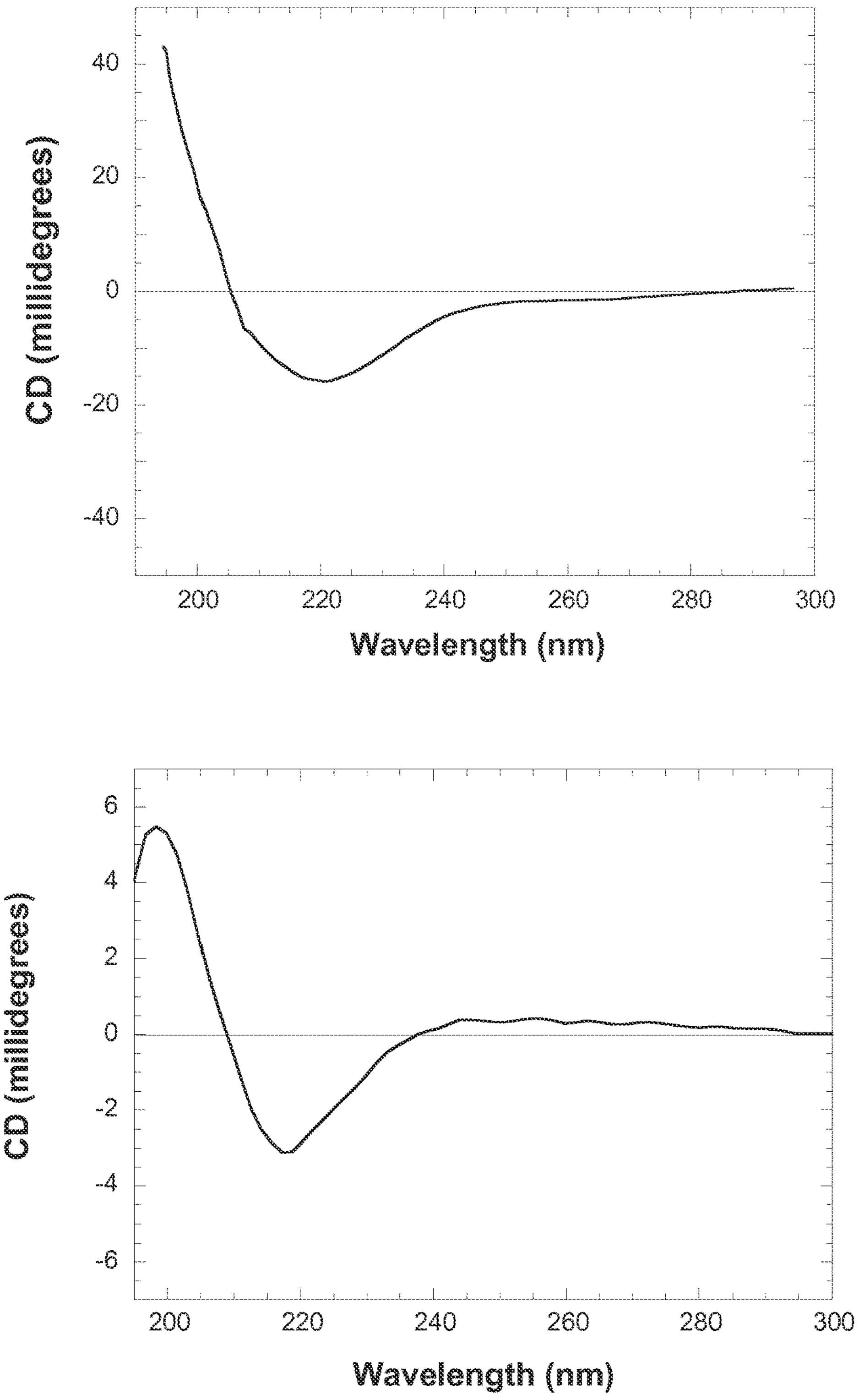
FIG. 8 shows circular dichroism spectra of (A) SBAFP-m1 in 10 mM sodium phosphate, pH 7.8 and (B) RGAFP-m1 in 10 mM sodium phosphate, pH 7.8. The spectrum for SBAFP-m1 was recorded in a 1 cm path length cell, while that for RGAFP-m1 was recorded in a 0.1 cm path length cell. Both spectra show a single minimum at ~220 nm indicative of predominantly β-sheet secondary structure for both proteins.

The length of the fibrils can be controlled, for example through a variety of approaches including varying of the temperature (e.g., between 5° C. to 45° C.), by following the incubation with sonication, by the addition of inhibitors of polymerization, or by modifying the buffer solution. For example, fibrils of several microns can be routinely produced. Alternatively, shorter fibrils (e.g., 100-200 nm) can be produced upon sonication (panel at lower right in FIG. 8).

Use of Modified Beta Solenoid Proteins as Scaffolds

In the practice of the present invention, one skilled in the art can refer to technical literature for guidance on how to design and synthesize a scaffold including the literature cited herein. For example, although the present invention relates to mBSP scaffolds. The mBSPs described above can be engineered to function as a scaffold for attachment and specific spatial arrangement of a number of nanomaterials. Methods of using protein scaffolds to prepare nanomaterials of desired properties are known (see e.g., U.S. Pat. No. 8,201,724, and US2009/0194317). A schematic of a scaffold of the invention is shown in FIG. 1.

The invention takes advantage of the ability of the mBSPs of the invention to self-assemble into 1, 2, and 3 dimensional scaffolds for template growth of nanoparticles. The described examples can be used in a variety of contexts, for example to grow photovoltaic, thermoelectric, catalytic, and photocatalytic devices.

One of skill will recognize that the amyloid fibrils of the invention can be arranged in any desired, pre-determined pattern, depending upon the particular application. For example, fibrils can be arranged in a repetitive pattern, and/or in which the pattern is substantially parallel. In some embodiments, the fibrils are configured with a directional order.

In some embodiments binding of scaffolds to surfaces can be achieved via similar strategies to the templating discussed above. In particular, binding can be achieved by: (a) sulfur chemistry of unoxidized cysteine or lysine side chains to bind to thiols decorating a prepared surface; and (b) peptide bond chemistry to link exposed lysine side chains to carboxyl groups decorating a prepared surface.

In certain circumstances, the surface can be mica, silicon, glass, or a transparent conducting oxide, for example, FTO or ITO. In some embodiments, the surface can be poly-L-lysine coated mica (0001) surfaces.

In certain circumstances, the functionalized substrate can include an aminopropylsilane functional group, a carboxyethylsilane functional group, an epoxide functional group, or an amine functional group and a carboxylic acid functional group, or combinations thereof. In certain circumstances, the functionalized substrate can be positively charged.

Using the nanoscale templating embodiments described above allows for the generation of ordered arrays of nanoscale catalysts with variable spacing controlled by the size of fused monomers and/or the end controlled linear aggregation. Additionally, catalytic nano-structures can be developed by controlling elemental identity and geometrical arrangement of molecular catalytic moieties.

As noted above, a wide variety of nanoparticles can be attached to the scaffolds of the invention. The nanoparticles can be precursor inorganic materials that form the desired nanomaterial such as inorganic nanocrystals. From these inorganic nanoparticles, inorganic nanomaterial can be formed consisting essentially of the fused inorganic nanoparticles upon substantial removal of the scaffold. The nanomaterial of the invention can comprise or consist essentially of materials such as, for example, semiconducting materials, whether doped or undoped; metallic materials; metal oxide materials, and magnetic materials. Various oxide materials including silica and alumina can also be used. In a typical embodiment, the nanomaterials prepared according to this invention conduct electricity as an electrical conductor, are semiconductive (whether inherently or via doping), transmit light, are magnetic, or possess some other technologically useful property. Other properties of the nanomaterials include ferroelectric properties, piezoelectric properties, converse-piezoelectric properties, and thermoelectric properties.

In many embodiments, the nanomaterial is a semiconductor. Semiconductor materials are well known to those of skill in the art and can be, for example, alloys including IV-IV Group (e.g., Si, Ge, $Si_{(1-x)}$, $Ge_x$), III-V Group binary (e.g., GaN, GaP), III-V Group ternary (e.g., $Ga(As_{1-x}P_x)$), II-VI Group binary (e.g., ZnS, ZnSe, CdS, CdSe, CdTe), IV-VI Group binary (e.g., PbSe), transition metal oxides (e.g., $BiTiO_3$), and combinations thereof.

In certain circumstances, the nanomaterial precursor can include a metal oxide compound. The metal oxide can include a manganese oxide, a magnesium oxide, an aluminum oxide, a silicon oxide, a zinc oxide, a copper oxide, a nickel oxide, a cobalt oxide, an iron oxide, a titanium oxide, yttrium oxide, a zirconium oxide, a niobium oxide, a ruthenium oxide, a rhodium oxide, a palladium oxide, a silver oxide, an indium oxide, a tin oxide, an lanthanum oxide, an iridium oxide, a platinum oxide, a gold oxide, a cerium oxide, a neodymium oxide, a praseodymium oxide, an erbium oxide, a dysprosium oxide, a terbium oxide, a samarium oxide, a lutetium oxide, a gadolinium oxide, a ytterbium oxide, a europium oxide, a holmium oxide, a scandium oxide, or a combination thereof.

The nanomaterial of the invention can also be crystalline. The material can have one or more crystalline domains. The crystalline phase can be either the thermodynamically favorable crystalline state or a crystalline state which is not thermodynamically favorable but is locked in by the relative orientation of the crystalline nanoparticles before fusion. The nanoparticles can be oriented in any manner. For example, the crystallographic axis of the nanoparticles can be oriented with respect to the surface of the mBSP scaffold. The thermal treatment can be varied to achieve a desired crystalline structure, or to covert polycrystalline structures to single crystalline structures.

In one embodiment, the invention provides a method of making a nanomaterial using the mBSPs of the invention. In a typical embodiment, the mBSP scaffold has a predetermined spatial orientation (e.g., one dimensional or two dimensional). The scaffold comprises a plurality of binding sites along its length and/or at each end. The binding sites are sites at which the desired nanoparticles are bound. The binding sites can be the same or different so that one or more nanomaterial precursor can be bound. For example, different binding sites can be achieved by using different monomers that self-assemble in a predetermined pattern. The nanomaterial precursor is contacted the scaffold to form a scaffolded precursor composition. Next, the scaffolded precursor composition is treated to form the nanomaterial having the desired spatial orientation.

The step of treating the precursor to form the nanomaterial will depend upon the material used. In many embodiments, a thermal treatment step is used, as is known in the art. The treating step may also comprise a chemical reduction of metal precursor salts. The scaffold can be removed before or after the treating step. In general, the reaction and the precursor materials should be compatible with the scaffold.

The temperatures and times for the thermal treatment step are known in the art. In general, the melting temperatures and annealing behavior of the materials will be considered in selecting temperature. For example, temperatures of about 100° C. to about 1,000° C. can be used. Thermal treatment can be used to fuse the nanoparticle precursors into a single structure and also to remove the scaffold. The temperature can be selected to achieve a desired crystalline phase which may be a low energy phase or a high energy phase. In general, higher temperatures (e.g., above about 500° C.) can be used to ensure the scaffold is completely removed. Lower temperatures (e.g., below about 300° C.) can be used to maintain the scaffold. The time of the thermal treatment can be routinely determined by one of skill. Preferably, the temperature and time for thermal treatment can be adjusted to achieve the optimum balance for nanoparticle fusion while reducing undesired effects such as oxide formation.

The scaffolds of the present invention can be used in a variety of different commercial applications. For example, one dimensional scaffolds can be used to produce nanowires in applications requiring electrical conductivity or semiconductivity at the nanoscale, such as fuel cells, thin film batteries, supercapacitors, photovoltaic devices, LEDs, chemical and biological sensors, and the like.

In the example of photovoltaic devices a multiexciton photovoltaic device with nanoparticle orientation enabled by the templating principles of the mBSP arrays of the invention can be prepared. In these embodiments, each of the components of device can be precisely placed in the correct orientation with respect to the other components to produce the device. The mBSP self-assembled scaffolds of the invention can also be used to prepare thermoelectric devices. By employing the end-controlled specific templating of nanoparticles an embodiment of a thermoelectric strip for heating or cooling with templating of n-type nanoparticles on one side and p-type nanoparticles on the other side can be produced The mBSP self-assembled scaffolds of the invention can also be used for catalytic devices. It is well known that certain colloidal or nanoscale minerals based upon transition metal oxides can serve as effective catalysts for a number of reactions, such as splitting of water to yield hydrogen under solar illumination. Using the nanoscale templating of the present invention one of skill can prepare ordered arrays of these nanoscale catalysts with variable spacing controlled by the size of fused monomers and/or the end controlled linear aggregation approach described above.

The scaffolds of the invention can also be used to create arrays of specific enzymes for which (i) co-localization and (ii) immobilization can yield improved performance. For example, a three step enzymatic pathway on a one dimensional scaffold can be achieved by attaching each enzyme in the pathway to a different monomer and using end controlled linear aggregation to ensure the specific co-localization of the enzymes on the scaffold.

The scaffolds can also be used for adsorption of atoms and molecules in environmental contexts. For example, two- and three-dimensional mBSP scaffolds can be used to nucleate specific adsorption of atoms and molecules in environmental contexts for applications such as (i) gettering of heavy metal ions for remediation of contaminated environments, and (ii) extraction of uranium and thorium complexes from seawater for application of nuclear fuels. The scaffolds can also be engineered to template growth of minerals such as calcium carbonate. This application can enable such scaffolds to be added to existing cement formations as crack strengtheners.

Examples

The following examples are offered to illustrate, but not to limit the claimed invention.

Methods

Molecular Dynamics Simulations

All molecular dynamics simulations of both designed peptides were performed using the AMBER 12 package[36] at our custom built STRIDER GPU cluster at U C Davis. The ff12SB parameter set was employed with a time step of 0.002 ps and fully constrained bonds to hydrogen atoms. The aqueous peptide environment was simulated explicitly with TIP3P water at constant pressure, in a long, rectangular box with periodic boundary conditions (PBC). In simulating long, fibrillar multimers, a novel adaptive box algorithm was employed to economize the computation (avoiding an exceedingly large solvation geometry) all while maintaining a consistent solvent environment: (i) The minimum pairwise distance of the macromolecule (solute) with all of its periodic images was regularly recomputed, specifically anticipating rotational drift. (ii) When this distance decreased below a cutoff of 15 angstrom, waters beyond this distance from any solute atom were stripped; the solute and close waters were reoriented in a new rectangular box wherein the box boundaries were at least 20 angstrom from any solute atom; and this box was resolvated with TIP3P waters of an appropriate density for the fixed pressure. (iii) The simulation was recommenced, accepting a picosecond-scale duration to accommodate the re-equilibration of outer-shell waters in the new periodic box. The simulations for the SBAFP-m1 and RGAFPm2 fibrils were carried out for 20 ns with five different random number seeds for the Langevin thermostat.

β-Sheet content was measured from simulation time series by using VMD[37] to count the number of residues within the typical β-sheet secondary structure region of the Ramachandran plot of φ-ψ torsion angles (i.e., $-180°<\varphi<0°$, $-180°<\psi<-150°$, and $-180°<\varphi<0°$, $60°<\psi<180°$).

The height profiles of the monomers for comparison with AFM experiments were obtained as follows. First, to remove any inherent twist in the monomers, we constrain Ca atoms on one side of the monomer to lie in a plane and use energy minimization within the AMBER suite to relax this constrained structure. Then, each monomer was rotated such that its helical axis is aligned along the x-axis. The monomers were then rotated about x-axis at 10-degree angle intervals. At each rotation the maximum z-coordinate height difference was measured for 5 Å thick slabs along the length of the helical axis. The average and standard deviations of this height along the length of the monomer was then obtained. Only heavy atoms were used for the height measurements.

Protein Expression, Purification, and Folding

The SBAFP-m1 and RGAFP-m1 genes in pET28a were procured from Life Technologies (Grand Island, N.Y.). Proteins were expressed in *E. coli* BL21 (DE3) cells. For SBAFP-m1, 1 L cultures were inoculated with overnight cultures and grown at 37° C., until $OD_{600}$ reached 0.9-1.0. Cultures were cooled on ice for 30 min after which isopropyl β-D-1-thiogalactopyranoside (IPTG) was added to a final concentration of 1 mM. Protein expression proceeded at 30° C. for 3 h. and cells were collected via centrifugation and resuspended in lysis buffer (50 mM Tris-HCl, pH 8.0, 100 mM NaCl, 5 mM EDTA and 0.5% Triton X-100). Cells were lysed by sonication and soluble and insoluble fractions separated by centrifugation. Insoluble inclusion bodies were purified by repeated sonication in lysis buffer without Triton X-100 and centrifugation, total of four times. The purified inclusion bodies were resuspended in folding buffer (100 mM Tris, 50 mM glycine, pH 8.0) and were added dropwise into denaturing buffer (100 mM Tris-HCl, 50 mM glycine, 8.5 M urea, pH 8.0) at 4° C. with stirring overnight. Denatured SBAFP-m1 was purified on Fast Q Sepharose anion exchange column (GE Healthcare Lifesciences, UK). The loading buffer was 50 mM Tris-HCl, 10 mM NaCl, 8 M urea, pH 8.0 while the elution buffer was identical except for being supplemented with 500 mM NaCl. Elution used a linear gradient. Purified SBAFP-m1 was concentrated using Amicon centrifugal devices (EMD Millipore. Germany) with a molecular weight cut-off of 3500 Da. Purified, concentrated SBAFP-m1 was refolded by stepwise dialysis out of urea using dialysis membrane with a molecular weight cut-off of 3000 Da and into 0.1 M Tris-HCl, pH 8.0 at 4° C. Each day the concentration of urea was decreased by 1 M until it reached zero.

The WT SBAFP gene in pET20b was acquired from the Davies lab and expressed according to the published protocol with minor changes.[33] Briefly, protein was expressed in BL21(DE3) *E. coli* cells in LB with IPTG induction when cell density reached 0.9 at 600 nm. Cells were collected via centrifugation and resuspended in a lysis buffer of 10 mM Tris-HCl, pH 9.0, 1 mM EDTA and 10 mM 2-mercaptoethanol. Cells were disrupted by sonication and IB's denatured in lysis buffer containing 8 M urea and allowed to stir overnight at 4° C. Crude, denatured SBAFP was purified like SBAFP-m1 with buffers supplemented with 10 mM 2-mercaptoethanol to keep cysteines reduced. Dialysis buffer for refolding was supplemented with 2% w/v glycerol.

The RGAFP-m1 and WT RGAFP proteins were expressed by inoculating a 1 L culture with overnight cultures and grown at 37° C. until $OD_{600}$ reached 0.9-1.0. Cultures were chilled in an ice-water bath for 20 min followed by IPTG addition to 0.5 mM. Protein expression continued at 18° C. for 20 h. The cells were pelleted by centrifugation and resuspended in PBS, pH 7.4 (10 mM sodium phosphate, 138 mM NaCl, and 2.7 mM KCl) followed by freezing at −80° C. The frozen cell pellet was thawed at 37° C. and boiled for 10 min to lyse the cells. After a 2 h. cooling period, RGAFP-m1 was sonicated extensively. DNAseI (Worthington Biochemical Corp., Lakewood, N.J.) was added to a final concentration of 1.6 μg/mL to the sonicated sample and incubated for 40 min followed by heat inactivation of the DNAseI by boiling at 100° C. for 10 min. The sample was allowed to cool to 4° C. and dialyzed into PBS with 6-8 kDa dialysis tubing (Spectrum Labs, Irving, Tex.). As a final purification step, the dialyzed protein was loaded onto a Fast Q Sepharose anion exchange column (GE Healthcare Lifesciences, UK) and washed with PBS pH 7.4. The elution buffer was supplemented with 0.5 M NaCl. Fractions containing proteins were pooled and dialyzed into PBS buffer before incubating samples at 37° C. for fibril formation.

The boiled cell lysate of WT RGAFP was purified using a nickel-NTA resin pre-equilibrated with binding buffer (50 mM Tris-HCl, 0.5 M NaCl, 5 mM Imidazole, pH 7.5) in a 10 cm×1.5 cm column. The bound WT RGAFP was washed with 10 column volumes of binding buffer and the protein eluted with elute buffer (50 mM Tris-HCl, 0.5 M NaCl, 200 mM imidazole, pH 7.5). Fractions containing protein were pooled and dialyzed into PBS using a 6-8 kDa dialysis membrane tubing. Protein concentrations for both RGAFP-m1 and WT RGAFP were determined with the bicinchoninic acid assay (Thermo Scientific, Rockford, Ill.).

Amyloid Fibril Formation

Purified SBAFP-m1 at a concentration of 70 μM in 0.1 M Tris-HCl, pH 8.0 was transferred to an Eppendorf tube and incubated at 37° C. to promote fibril formation. Purified RGAFP-m1 at a concentration of 98 μM in PBS pH 7.4 was incubated at 37° C. in an Eppendorf tube until further analysis.

Thioflavin-T Fluorescence Assay

ThT fluorescence was measured as described.[45, 46] ThT stock solutions were prepared by dissolving ~2 mg of ThT (Sigma-Aldrich) in 2 mL of PBS, pH 7.4 and filtered through a 0.22 μm filter. Stock concentrations were determined using an extinction coefficient of 26,620 $M^{-1}$ $cm^{-1}$ at 416 nm. A working 500 μM ThT solution was prepared from the stock solution. For the assay, SBAFP-m1 was added to a final concentration of 5 μM and ThT to a final concentration of 10 μM in PBS, pH 7.4. The emission spectrum was recorded from 465 nm to 565 nm with excitation at 450 nm. For the assay, all protein concentrations, except for RGAFP-m1, were added to a final concentration of 5 μM and ThT to a final concentration of 10 μM in PBS, pH 7.4. RGAFP-m1 was added to a final concentration of 1.8 μM due to a loss of protein after incubation. ThT data for RGAFP-m1 were normalized for the decrease in concentration.

Circular Dichroism

Protein secondary structure was analyzed using CD. For SBAFP-m1, the spectrum is a concentration-normalized combination of those for 0.02 mg/mL sample from 190 nm to 200 nm and 0.2 mg/mL sample from 200 nm to 300 nm in 10 mM sodium phosphate, pH 7.4, in a 1 cm cell at 25° C. Spectra were collected at a scan rate proportional to high voltage using an OLIS DSM 20 instrument. Reported spectra are an average of 5 scans. For RGAFP-m1, spectra were taken with 0.2 mg/mL sample in a 1 mm path length cell at 25° C. in 10 mM sodium phosphate, pH 7.4.

Dynamic Light Scattering

DLS measurements were performed using a Zetasizer NanoS (Malvern Instruments, Worcestershire, UK). Sample preparation for DLS measurements consisted of clarification by centrifugation at 13,000×g for 5 min. Protein concentrations were ~1 mg/mL in PBS pH 7.4. Measurements were made at either 4° C. or 37° C. depending on prior sample treatment. A protein refractive index of 1.450 and a water refractive index of 1.330 were used. Each reported value is an average of 10 acquisitions, each lasting 300 s. The averages and standard deviations of these 10 runs are reported.

Atomic Force Microscopy (A) Sample Preparation.

Pieces of 8.0 mm×8.0 mm×0.5 mm muscovite mica were cut and mounted on standard microscope slides using composite epoxy glue (5 Minute Epoxy, ITW Performance Polymers and Fluids, FL. USA). Before protein deposition, the top layer(s) of mica was peeled mechanically to expose fresh (0001) surfaces. For SBAFP-m1 or wild type WT SBAFP, 20 μl of sample in Tris buffer (100 mM, pH8.0) were deposited on the freshly exposed mica(0001) surfaces. After 5 min incubation, the surfaces were washed three times with 200 μl Tris buffer (100 mM, pH 8.0) to remove weakly bound proteins and fibrils. The samples were immediately imaged in the Tris buffer. Sample preparation for RGAFP-m1 or WT RGAFP followed similar protocols except for the surface coating and imaging medium. The freshly cleaved mica(0001) surfaces were coated with poly-L-Lysine, by dropping 80 μl 0.1% (w/v) poly-L-Lysine (Sigma P8920, MW 150-300 kDa) onto the surface, incubating for 5 min, then washing with MilliQ water. The surfaces were dried with clean air before protein deposition. The samples were imaged under ambient conditions.

(B) Imaging.

AFM was performed using an MFP-3D AFM (Asylum Research, Santa Barbara, Calif., USA). Most images were acquired using AC or tapping mode to minimize perturbation and damage to surface bound proteins and fibrils. The typical set point was at 70%-80% of original amplitude, and scan rate was 0.8-1 Hz. For imaging in aqueous media, two types of probes were used. The first was a Biolever A cantilever (BL-RC 150, Olympus, Japan). Its resonance frequency (f) was determined by the built in software of MFP3D AFM. The spring constant (k) was provided by the manufacturer. Typically, f~10 kHz and k~30 pN/nm. The second type was an MSNL E cantilever (Brucker, USA) with f~11 kHz and k~100 pN/nm. For imaging under ambient (dry) conditions, AC240 cantilevers (Olympus, Japan) with f~65-75 kHz and k~2.0 N/m were used.

Fibrilization Kinetics

Monomeric samples (10 μM) in 0.1 M Tris-HCl pH 8.0 were held at 4° C. in 15 mL capped plastic centrifuge tubes until polymerization was initiated by incubating at 37° C. with shaking at 250 rpm. At various times, the tube was homogenized on vortex mixer and a sample was removed for analysis by absorbance at 300 nm (turbidity). DLS, and ThT fluorescence. Before ThT analysis, the sample was centrifuged for 5 min at 12,000×g at room temperature. The soluble supernatant and the resuspended insoluble precipitate were separately analyzed with ThT as above. The soluble protein concentration in the supernatant was measure by absorbance at 280 nm before being used in the ThT assay.

Results and Discussion

Most amyloid fibrils used in the literature for engineering purposes, e.g. templating nanowire growth,[19, 20] are derived from naturally occurring proteins or peptides known to form amyloid fibrils under specific conditions. For example, nanowires have been previously grown on a prion variant from *Saccharomyces cerevisiae* known to self-assemble[19] as well as on an Alzheimer's β-amyloid diphenylalanine peptide.[20] These examples and various others in literature[22] exploit naturally occurring amyloid fibrils. Approaches from other groups use harsh conditions (e.g., treatment with concentrated hydrochloric acid at elevated temperatures for various days[23]) to produce self-assembled amyloid fibrils out of intrinsically non-amyloidogenic proteins like lysozyme.[30] Instead of using naturally occurring peptides already known to self-assemble or exposing a protein to harsh conditions, we propose here a rational design concept to render intrinsically non-amyloidogenic proteins with natural cross-β structure into proteins that readily self-assemble into amyloid fibrils under benign conditions.

Protein Design (A) Spruce Budworm Antifreeze Protein.

Here, isozyme 501 of the β-solenoid antifreeze protein from the spruce budworm (SBAFP; PDB entry 1M8N)[31] was used to engineer one-dimensional fibrils. The polypeptide backbone is triangular about the long axis of the helix (FIG. 1). The structurally homologous 2PIG PDB entry (FIG. 3) shows that the left-handed β-solenoid scaffold is tolerant to substitutions at the apices of the triangular scaffold, and therefore likely to be robust for materials engineering.

Figure 3:
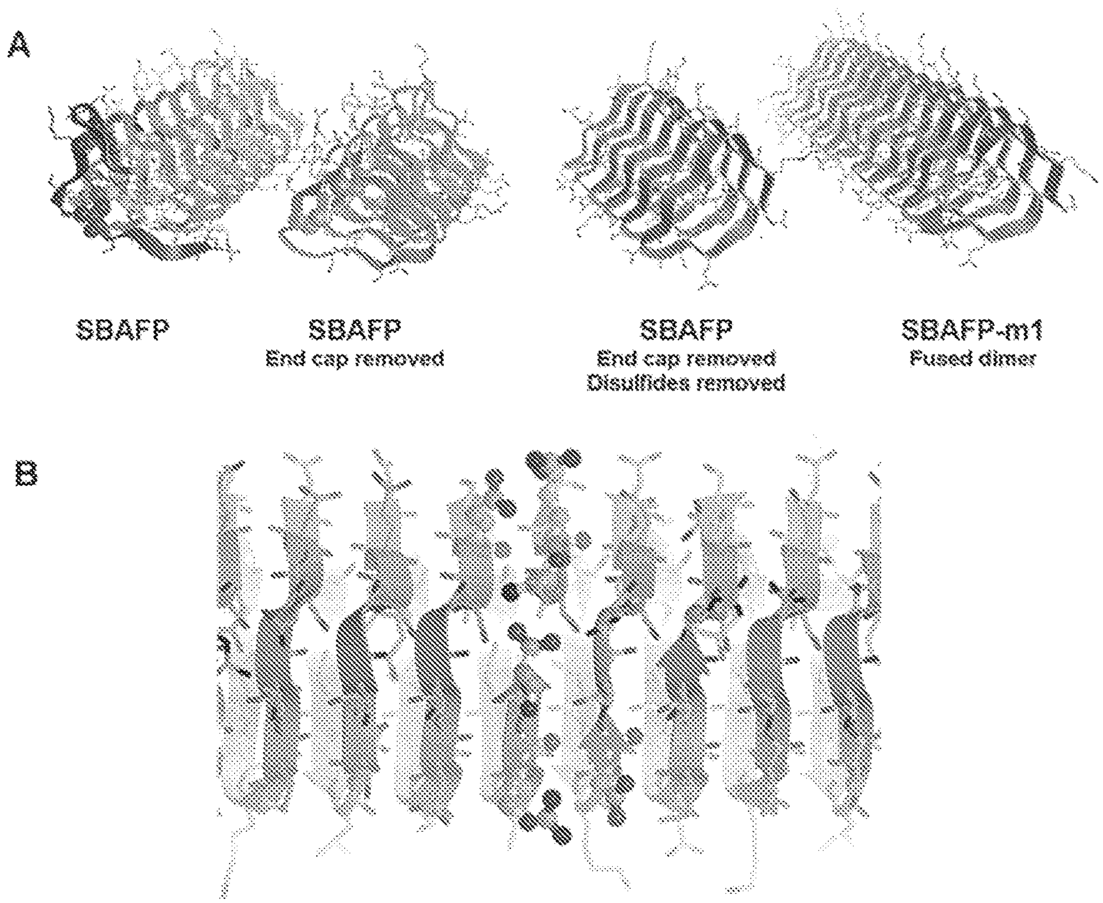
FIG. 3 shows stages in the design of SBAFP-m1. (A) The SBAFP wild type protein has a C-terminal capping motif shown in red. This was removed so that the N- and C-termini form a gapless interface when brought together. All cysteine residues (shown in space-filling on the second from the left) were changed to serines, eliminating the disulfide bonds. Two monomers were fused to form a larger protein that is more manageable genetically and biochemically. Finally, the monomer-monomer interface optimized, including the addition of two Arg/Glu salt bridges. (B) Close-up of the optimized interface between two SBAFP-m1 proteins. The N- and C-termini form a salt bridge, as do the two Arg/Glu pairs placed at the interface. These are shown in ball-and-stick representation.

There were two major considerations in the rational design of the first engineered protein, termed SBAFP-m1. The first was seamless and stable end-to-end interactions, and the second was ease of biochemical handling. The first was addressed as follows, and as illustrated in FIG. 3. The β-hairpin-like capping motif at the C-terminus of WT SBAFP was removed to give a clean C-terminus in the β-strand conformation (FIG. 3A). This required eliminating the last 21 residues. The N-terminus was modified by removing the first six amino acids present in the crystal structure of SBAFP. To avoid a heterogeneous N-terminus, Met-Ala were used for the first two amino acids of the SBAFP-m1 sequence (SEQ ID NO:1). The *E. coli* methionine aminopeptidase has a strong preference for small amino acids such as alanine at the second position.[32] Thus, the Met-Ala sequence increases the likelihood that the N-terminal amino acid is homogeneously processed to Ala instead of a possible mixture of Met and a different second amino acid. This design gives a seamless interface between the N- and C-termini of successive monomers, as illustrated in FIG. 3B.

Two additional salt bridges were placed at the interface of the termini to increase the stability of the interaction between monomers. These are illustrated in FIG. 3B. As modeled, the end-to-end interface includes three salt bridge interactions: one between the N- and C-terminal ammonium and carboxylate groups, and two between the Arg/Glu side chain pairs introduced. These, along with the inter-monomer β-sheet hydrogen bonding, proved sufficient to keep the interface structure stable in MD simulations at 100° C. for 2 ns, and for 20 ns runs at 25° C. as described further below.

Figure 4:
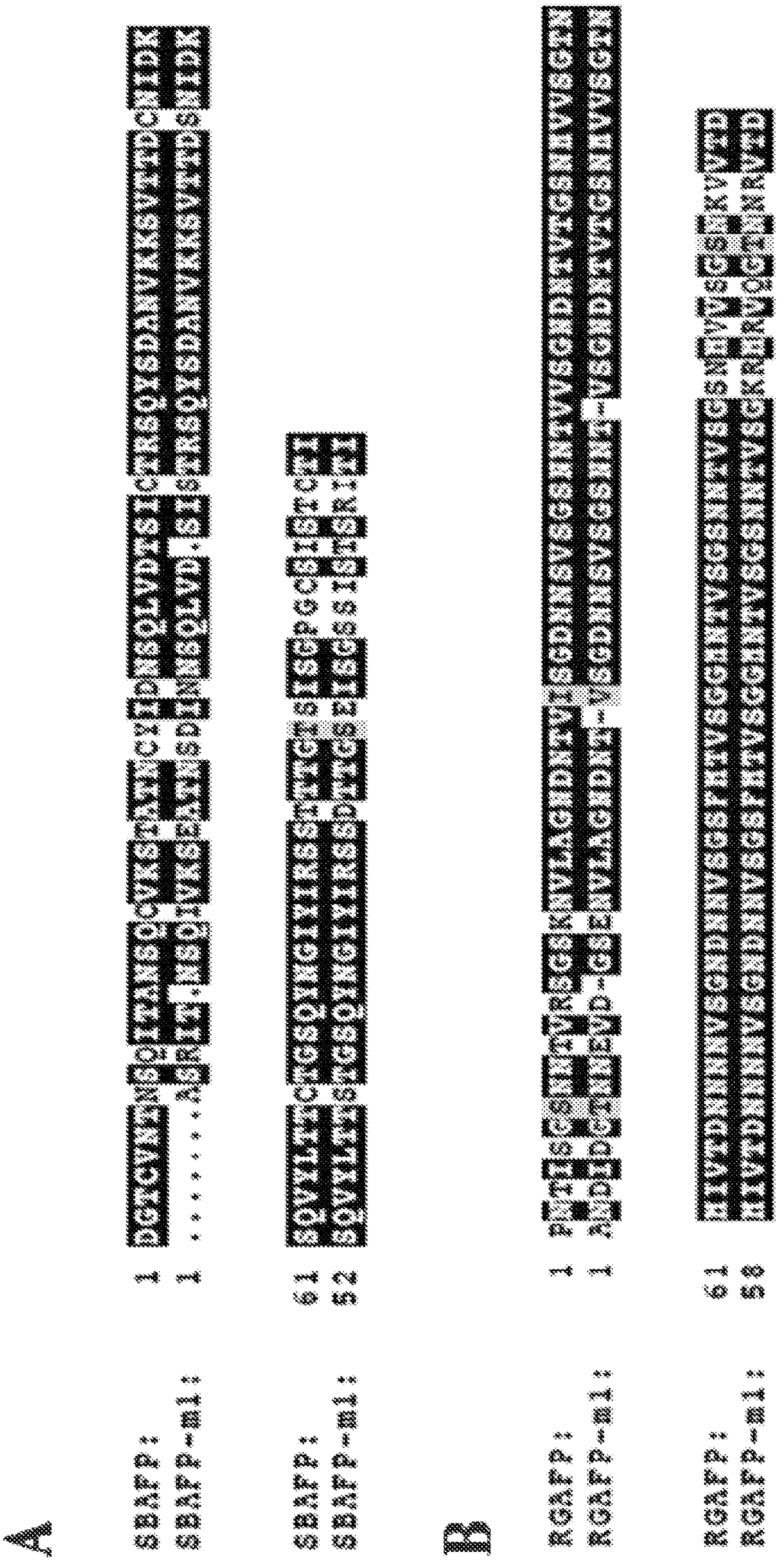
FIG. 4 shows (A) Sequence alignment between WT SBAFP (PDB entry 1M8N, SEQ ID No:3, residues 1-100) and the SBAFP-m1 protein (SEQ ID NO: 1) derived from it. Only the first half of SBAFP-m1 (itself composed of two fused monomers) was used in the alignment. The last 21 residues of 1M8N were deleted in the design of SBAFP-m1 (SEQ ID NO: 1) and the first Met are not shown in the alignment. (B) Alignment between WT RGAFP (SEQ ID NO:4, residues 5-118) and RGAFP-m1 (SEQ ID NO:2), which has a total of three deletions and 13 mutations, compared to WT RGAFP (SEQ ID NO:4).

WT SBAFP has a total of five disulfide bonds. These undoubtedly stabilize the folded protein, yet disulfides often present difficulties to high-level expression of recombinant proteins in *E. coli* and their subsequent handling. Nevertheless, recombinant expression of WT SBAFP in *E. coli* was previously achieved and reproduced here (see Methods),[33] but the expression levels are modest. Modeling the replacement of all the cysteines by serines showed a good steric fit and enabled hydrogen-bonding interactions to partially replace the disulfide bonds stabilizing interactions. An alignment of sequences summarizing deletions and mutations between WT SBAFP (SEQ ID NO:3) and SBAFP-m1 (SEQ ID NO:1) are presented in FIG. 4A. Molecular dynamics simulations also showed the Cys-to-Ser mutant stable at 25° C. for 20 ns. Therefore, the Cys-to-Ser mutations were kept in the design. The cysteine-less design also has the advantage that future engineering efforts can employ the introduction of a unique cysteine to enable chemically specific modification of the protein.

The alterations described above left a relatively small protein of 90 amino acids. For ease of recombinant expression, purification, and functionalization of the protein, two of the 90 amino acid monomers were genetically fused together to give a single contiguous protein of 180 amino acids in length.

(B) Ryegrass Antifreeze Protein.

Figure 5:
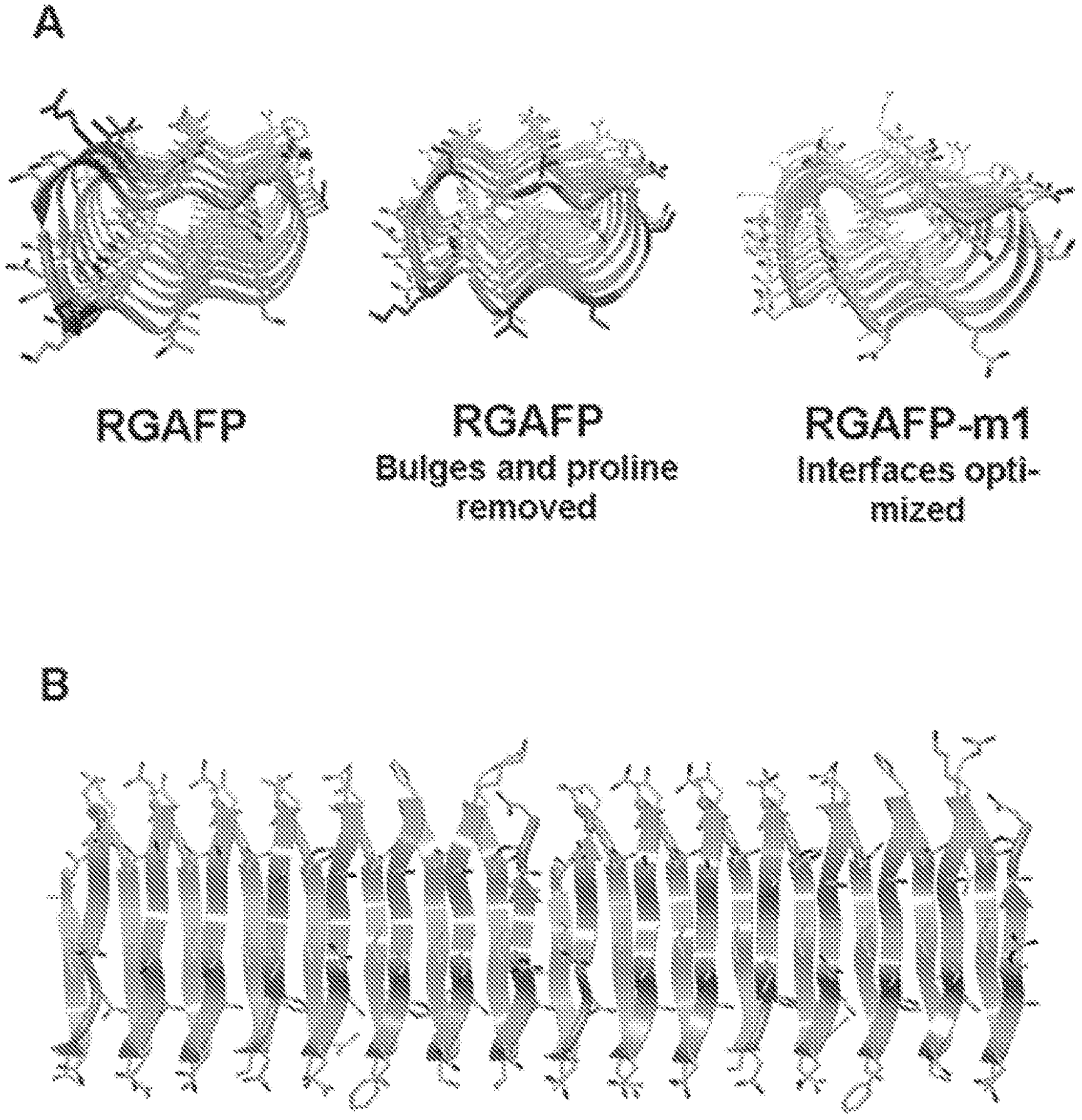
FIG. 5 shows stages in the design of the RGAFP-m1. (A) The N-terminal proline and amino acids causing the bulge (marked in red in the left structure) were deleted. Next, amino acids at the monomer interface (marked in red in the center structure) were mutated to optimize binding interactions. (B) Close up of end-to-end dimer interface of RGAFP-m1.

As illustrated in FIG. 5, the same basic design concepts used for SBAFP-m1 were applied to a ryegrass (*Lolium perenne*) antifreeze left handed β-solenoid protein (RGAFP, PDB entry 3ULT)[34] with the addition of using FoldIt[35] to optimize the interface. In contrast to SBAFP, which has a triangular cross section with three β-sheet faces, RGAFP has two β-sheet faces in a rectangular arrangement along the long axis of the β-helix. The structure has 8 β-sheet rungs, each containing 14-15 amino acids per turn, and an exceptionally flat β-sheet on the ice-binding face. There is an additional amino acid present in the first three rungs, causing a bulge at the N-terminus of the protein structure (FIG. 5A). These amino acids were removed to regularize the β-helix. Residues 1-4, which are missing in the crystal structure were excluded from the designed protein, termed RGAFP-m1. Additionally, residue 5 (Pro), which might interfere with polymerization was mutated to Ala, which additionally facilitates a homogeneous N-terminus as with the SBAFP-m1 design.

To engineer an idealized interface, a dimer model (FIG. 5B) was used. Residue Lys110 appeared to hinder interface formation and hence was mutated to Asn. As with the design of SBAFP-m1, an Arg/Glu salt bridge was added at the interface. To further strengthen the interaction between monomers at the binding interface, FoldIt[35] optimization was used as follows. The last 16 residues of the first monomer and the first 16 residues of the second monomer were allowed to mutate to get the best FoldIt score. This resulted in 10 mutations that largely increased the overall charge of the proteins at the interface. Thus, a total of 13 mutations, summarized in FIG. 4B, were incorporated in the design. Further testing using molecular dynamics simulations showed that the modeled interface was stable for 20 ns at 25 C.

Molecular Dynamics Simulations

The designed proteins were tested using MD simulations for 20-ns at constant pressure and temperature (25° C.) using AMBER 12[36] suite (see Methods). Both individual monomers and longer 11-unit multimers were analyzed for stability in MD simulations. Monomer simulations determined the inherent stability of each design, particularly with respect to the modifications of the sequence at the termini. A concern was that new steric and electrostatic interactions might lead to local instability of the β-helical motif, which could disrupt polymerization. In the case of SBAFP-m1, the monomer simulation also probed the viability of the novel inter-monomer interface, with fused identical 90-residue segments used as proxies, where de-registry or layer separation of the ideal motif might have occurred.

Figure 6:
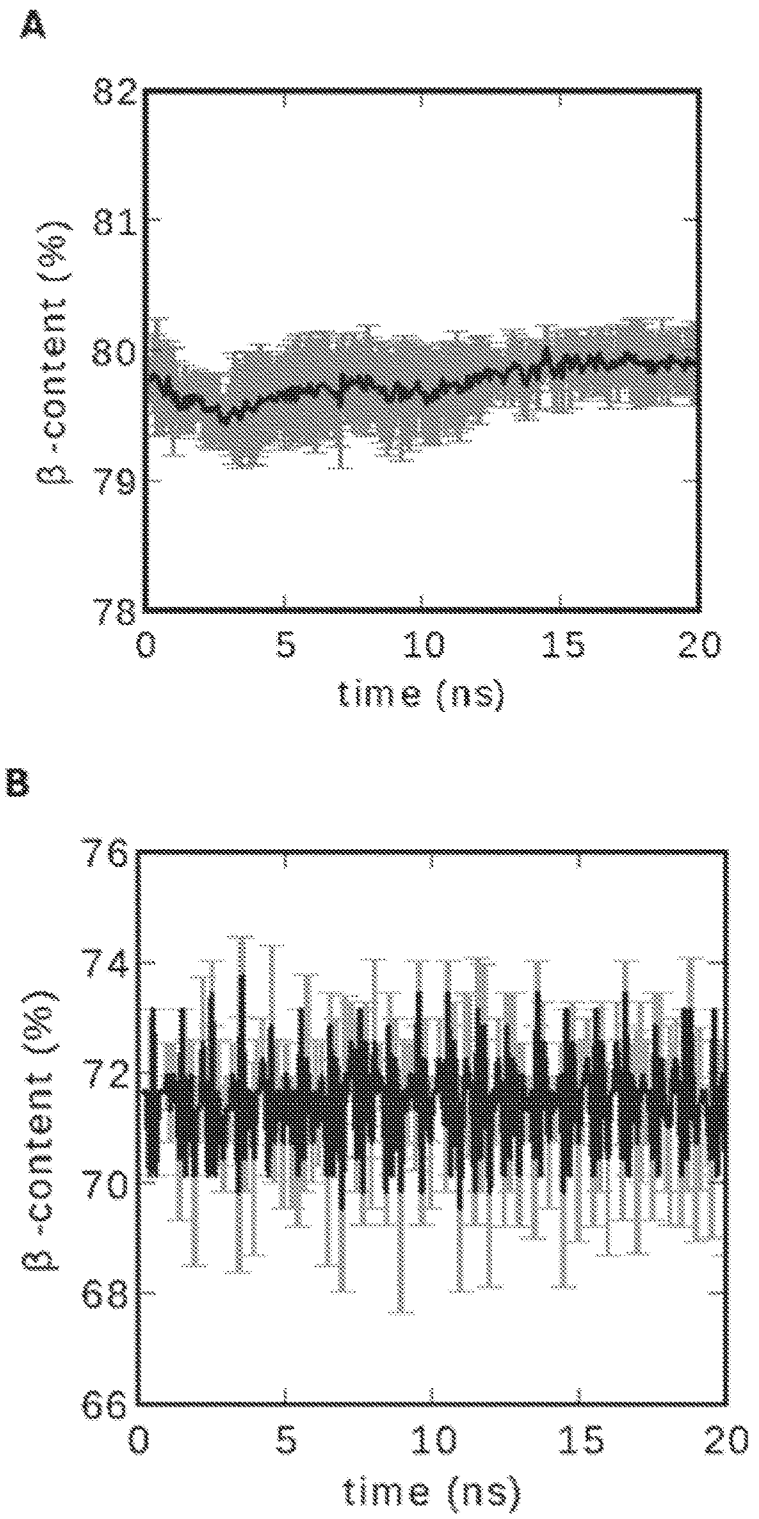
FIG. 6 shows β-Sheet content vs. time during fibril simulations. (A) SBAFP-m1 (B) RGAFP-m2. The data are averaged over five different runs each with random number seeds of the Langevin thermostat in the AMBER12 simulation suite.[36] The β-content was determined by counting residues in the β-sheet region of the Ramachandran plots using VMD.[37]

Models of eleven-unit multimers were also constructed to observe the behavior of ideal fibrils. Here, a sample often dimer interfaces could be observed simultaneously for defects or instability, along with the macroscale super-helical tendencies of a long polymeric fibril. Molecular dynamics simulations demonstrated that both designs were stable out to 20 ns. A measure of this is seen in FIG. 6 where we plot the β-sheet content of simulated fibrils over time, averaged over five different runs for the SBAFP-m1 fibril and the RGAFP-m2 fibril. The latter is similar in design to the experimentally studied RGAFP-m1. The β-sheet content is determined by counting all residues within the β-sheet region of the Ramachandran plot (for further details see the Methods section) within the Visual Molecular Dynamics program (VMD).[37] For the idealized three-sided structure, this yields 80% β-sheet content (twelve β-strand residues per 15 residue rung), and for the idealized two-sided structure this yields 70% (ten β-strand residues per 14 residue rung). The monomeric form retained all native β-helical contacts, including those corresponding to terminal sequence segments that one might expect to separate or fray. Simulations of polymer fibrils showed that all dimer interfaces remained intact, and imperfections in monomer docking during the model construction process became annealed into seamless registry.

Figure 7:
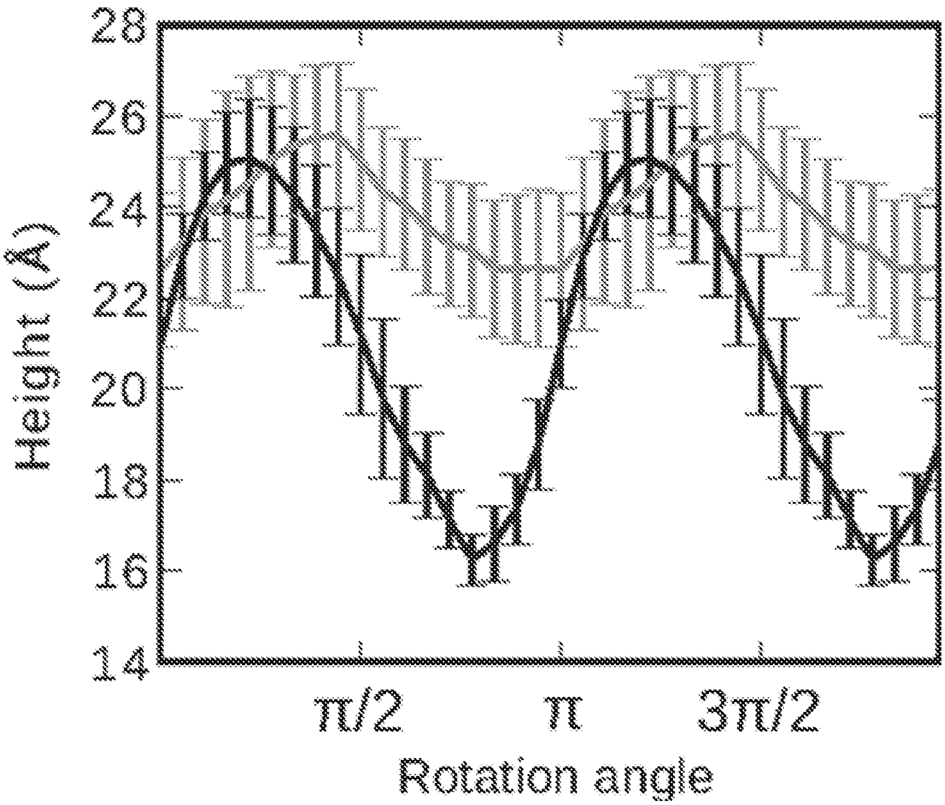
FIG. 7 shows height profile of SBAFP-m1 (gray) and RGAFP-m2 (black) monomers. For each case, the height minimum above a constraining surface corresponds to having a face parallel to and in contact with the surface. The maximum corresponds to having a line contact with an edge such that a face is perpendicular to the surface.

Another role for the simulations is to provide analyses of possible height profiles of fibrils to compare with the AFM topographic information. Note that this variation is mainly due to the triangular and rectangular cross-sections of the proteins. FIG. 7 shows height curves for monomers of SBAFP-m1 and RGAFP-m2 found using the untwisted monomers. The SBAFP-m1 monomer has a mean height ranging from 2.25-2.55 nm, while the RGAFP-m2 monomer has a height variation between 1.6-2.6 nm.

Taken together, the simulations, carried out in advance of the experimental fibril synthesis, portended the experimental finding that the designed β-solenoid proteins form stable amyloid fibrils, and allowed us to exclude several intermediate designs in the process. Also, simulations provide important height profiles for comparison to AFM data to provide corroborating evidence that the observed fibrils have the desired structure.

Protein Expression, Purification, and Folding

The *E. coli* codon-optimized genes for both SBAFP-m1 and RGAFP-m1 were procured from Life Technologies The SBAFP-m1 variant expressed well in *E. coli* BL21(DE3)

from the pET28a vector, although it was found almost completely in inclusion bodies (IBs). The protein was purified using a protocol of repeated IB washing, denaturation in 8.5 M urea, and purification by anion exchange chromatography (see Methods).[38] Purified, unfolded protein was folded to its native state by stepwise urea removal via dialysis. Generally, a yield of 30-40 mg of pure protein per liter of growth medium was obtained. Once the protein was purified and refolded, it was placed in an incubator at 37° C. to allow fibril formation. Expression of the naturally occurring SBAFP followed a literature procedure, with minor changes detailed in the Methods section.[33]

The RGAFP-m1 gene in pET28a and WT RGAFP gene in pET24a were expressed in *E. coli* BL21 (DE3) cells. Whole cells were lysed by boiling for 10 min, releasing the heat-stable RGAFP-m1 and WT RGAFP into the soluble fraction. This was followed by a 2 h cooling period to room temperature to refold the protein and storage at 4° C. The heat stable properties of WT RGAFP are retained in RGAFP-m1, as shown in FIG. S1B. A yield of ~10 mg of pure RGAFP-m1 per liter of growth medium was obtained. WT RGAFP gave a yield of ~50 mg of pure protein per liter of growth medium. As with SBAFP, both RGAFP-m1 and WT RGAFP were incubated at 37° C. to promote fibril growth.

Spectroscopic Characterization (A) Mass Spectroscopy.

SBAFP-m1 has a calculated molecular mass of 19,397 Da with the N-terminal Met and 19,265 Da without it. ESI-MS analysis gives a molecular weight of 19,267±4.8 Da, corresponding to the protein without the N-terminal Met, as desired. SBAFP-m1 runs on SDS-PAGE with an apparent molecular weight of 20 kDa.

The RGAFP-m1 protein has a calculated molecular mass of 11,410 Da with the N-terminal Met and 11,279 Da without it. ESI-MS analysis gives a molecular weight of 11,280±2.8 Da, again corresponding to the mutant without the N-terminal Met. RGAFP-m1 runs on SDS-PAGE with an apparent molecular weight of 25 kDa.

This MS data provides important confirmation that the sequences of the proteins produced correspond exactly to those designed and tested for stability. No modifications to the proteins were detected.

(B) Circular Dichroism.

The CD spectrum for SBAFP-m1 is presented in FIG. 8A. It shows a single peak at ~220 nm, suggesting a largely β-sheet structure. Deconvolution of the spectrum using the Contin[39] Set 4[40] program on the online DichroWeb[41] server gave the following estimates for secondary structure content: 4% α-helix, 64% β-sheet/turn and 32% random coil. Simulation gives 80% β-sheet structure, per FIG. 6. This may indicate somewhat less stability for the experimental fibrils than expected by simulations. The SBAFP model has no α-helix, 89% β-sheet, 3% turns, and 8% coil as calculated by YASARA.

The CD spectrum for RGAFP-m1 is presented in FIG. 8B. As with SBAFP-m1, it shows a single peak at ~220 nm, indicative of a largely β-sheet structure. Deconvolution of the spectrum using CONTIN-Set 4 gave a secondary structure content of 2% alpha helix, 63% β-sheet/turn and 35% random coil. Simulations give 72% β-sheet as shown in FIG. 6. The RGAFP model has no α-helix, 88% β-sheet, and 12% coil as calculated by YASARA.

The secondary structure assignments agree reasonably well between structural models and the CD deconvolutions. The average error in secondary structure assignment by the CONTIN software is ~5% for a structure and ~10% for β structure,[42] although this depends on the protein and the lowest wavelength used in analysis.[43] Additional evidence of extended β-sheet formation is presented below.

(C) Thioflavin-T Fluorescence.

Thioflavin-T is a small molecule commonly used for the detection of amyloid cross-β structure in peptides and proteins.[44, 45] The binding mechanism is not well understood but is thought to involve either binding into "channels" between outward facing side chains of β-sheets and/or ThT micelle formation.[46] Empirically, ThT fluorescence is significantly altered when it binds to cross-β structures: compared to ThT free in solution, the excitation maximum shifts from 385 to 450 nm in the presence of β-sheet fibrils, and the emission maximum changes from 445 nm to 482 nm.[47] This fluorescence shift has been used extensively to probe peptides for β-sheet secondary structure, primarily with amyloid fibrils such as those from Aβ(1-42),[47] insulin,[48] and immunoglobulin light chain variable domain SMA.[49]

Figure 9:
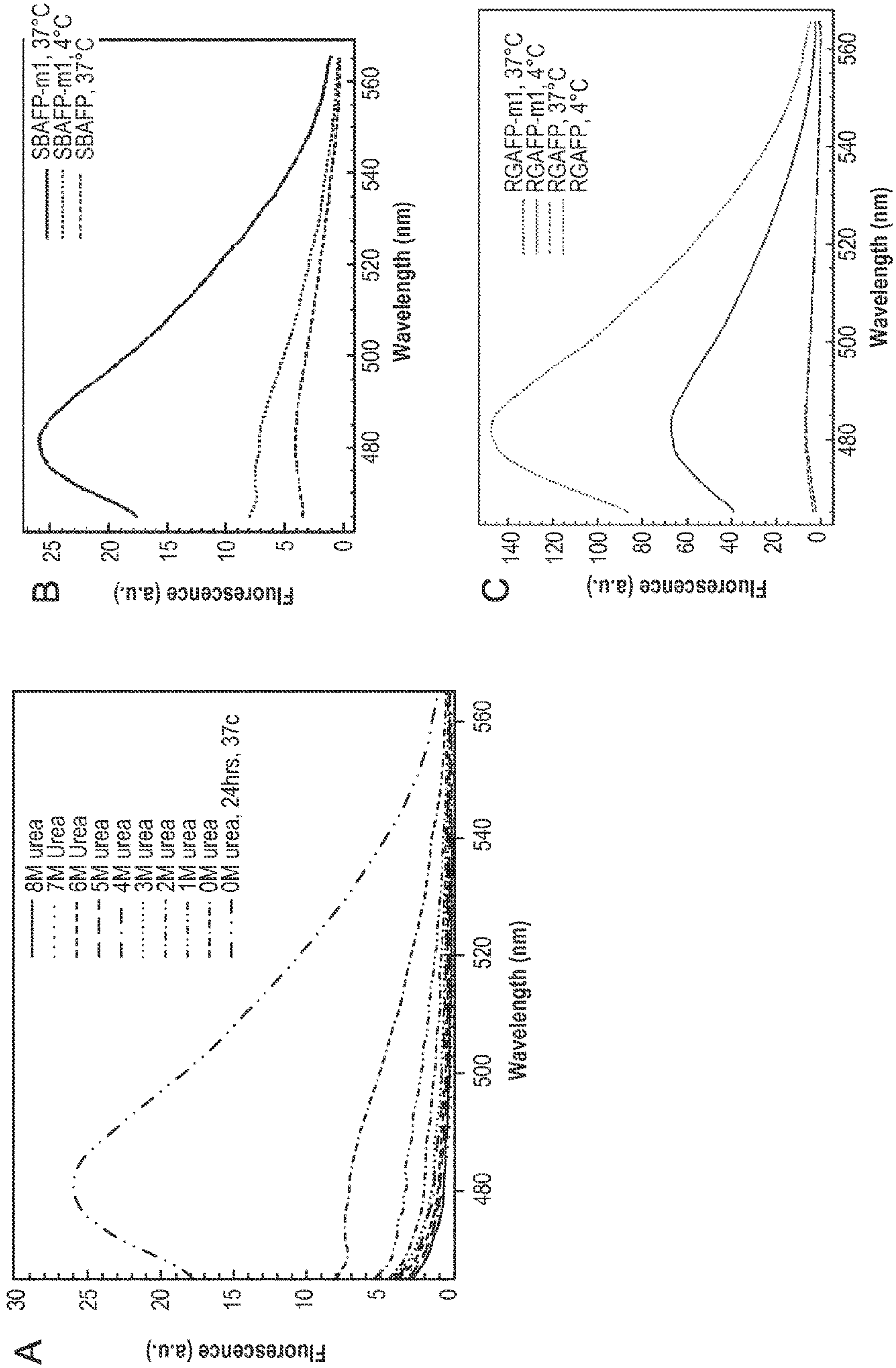
FIG. 9 shows ThT fluorescence analysis of SBAFP-m1 and RGAFP-m1. (A) ThT fluorescence assay of SBAFP-m1 as a function of urea concentration in 0.1 M Tris-HCl, pH 7.8. The samples were dialyzed against decreasing concentrations of urea in buffer over the course of 8 days. Incubation at 37° C. leads to an increase in β-sheet structure. (B) ThT fluorescence of SBAFP-m1 at 4° C. and 37° C. compared to WT SBAFP at 37° C. WT SBAFP has low fluorescence at 482 nm even after incubation at 37° C. (C) ThT assay comparing WT RGAFP to RGAFP-m1. WT RGAFP has low fluorescence both at 4° C. and 37° C., while RGAFP-m1 has significant fluorescence at 4° C. which increases with incubation at 37° C. as expected for the growth of amyloid fibrils. For the assay, final protein concentrations, except RGAFP-m1, were 5 μM and ThT was 10 μM in PBS, pH 7.4. RGAFP-m1 was added to a final concentration of 1.8 μM due to loss of protein on incubation at 37° C. ThT data for RGAFP-m1 were normalized for the decrease in concentration.

During the refolding of SBAFP-m1 by stepwise dialysis against solutions of decreasing urea concentrations, protein samples at each urea concentration were collected and analyzed for ThT fluorescence. FIG. 9A shows the ThT fluorescence of SBAFP-m1 at urea concentrations from 8 M urea to 0 M urea at 4° C., and SBAFP-m1 in the absence of urea after incubation at 37° C. for 24 h. There is a gradual increase in fluorescence at 482 nm for SBAFP-m1 as the urea concentration decreases; given the long time of incubation at 4° C. (8 days total to change from 8 to 0 M urea) the increase in ThT signal may arise from partial polymerization.

SBAFP-m1 at 4° C. gives low ThT fluorescence which is significantly above background and greater than that for WT SBAFP as shown in FIG. 9B. The larger signal from SBAFP-m1 compared to WT SBAFP implies a small degree of polymerization during the extended period (8 days) required for stepwise dialysis at 4° C. This is further evidence that SBAFP-m1 folds into the predicted β-helical structure after removal of urea by dialysis. Incubation of SBAFP-m1 at 37° C. for 24 h significantly increases ThT fluorescence at 482 nm, indicating formation of an extended β-sheet species that has higher ThT binding capacity or greater effects on the spectral changes of ThT. In general, incubation of amyloid-prone proteins and peptides at elevated temperatures is known to facilitate amyloid fibril formation.[50] The increase in ThT fluorescence with SBAFP-m1 after incubation at 37° C. implies that the elevated temperature promotes fibril formation since an identical sample held at 4° C. does not show the same large increase over 24 h (FIG. 9B). The kinetic studies discussed below confirm this.

The RGAFP-m1 protein has an increased ThT fluorescence emission peak at 482 nm compared to WT RGAFP as shown in FIG. 9C. Incubation of the WT RGAFP sample at 37° C. did not change the ThT emission intensity, suggesting that WT RGAFP does not form amyloid fibrils. RGAFP-m1 kept at 4° C. exhibits significant ThT fluorescence, albeit at a weaker intensity than the sample after incubation at 37° C.; this suggests some fibril formation at the lower temperature. This is also evidenced by the DLS data discussed below, which shows evidence for aggregates in the 4° C. sample. After incubation, fluorescence at 482 nm increases considerably, undergoing the same pattern seen with SBAFP-m1. This indicates the formation of longer amyloid fibrils with β-sheet conformation. Only weak fluorescence is seen for WT RGAFP both at 4° C. and after incubation at 37° C., indicating the changes made to the protein template are causing the controlled aggregation. Fibril formation for both SBAFP-m1 and RGAFP-m1 is further evidenced by DLS data, discussed below.

(D) Dynamic Light Scattering.

DLS measures the hydrodynamic size of species present in solutions and is a non-destructive method for investigation of self-assembly. Measuring the size of the species in solution by DLS complements AFM imaging in characterizing the size distribution of fibrils.

For SBAFP-m1, DLS measurements performed before incubation show a species having an apparent hydrodynamic diameter of 6.6±1.4 nm that constitutes ~99.8% of the sample, with the remainder consisting of minor species between 59 and 5560 nm in diameter. After incubation at 37° C. for 24 h, the species at 6.6 nm (presumably the monomer since the calculated diameter of gyration is ~4 nm for the unhydrated model) is absent. Larger species at 32±8 and 230±43 nm in apparent diameter are present. Thus, SBAFP-m1 may self-assemble to a minor extent at 4° C., while the monomer is absent and larger species are present after 24 h incubation at 37° C.

Dynamic light scattering results with RGAFP-m1 also show an increase in fibrils after incubation at 37° C. Before incubation, the sample consisted of species with apparent hydrodynamic diameters of 5.0±0.3 nm (~98.7%), 28±4 nm (~1.1%) and 143±40 nm (~0.2%). After incubation at 37° C., the monomer at 5 nm is absent, and a species with an apparent diameter of 268±48 nm constitutes the entire sample. The presence of small amounts of large species in the sample before incubation at 37° C. could either be due to polymerization at 4° C., as with SBAFP-m1, or the procedure by which RGAFP-m1 was purified and folded. Unlike SBAFP-m1, RGAFP-m1 was purified and folded by boiling followed by slow cooling to room temperature. This process gives the newly folded protein substantial time at both 4° C. and higher temperatures to undergo polymerization.

AFM Imaging

Figure 10:
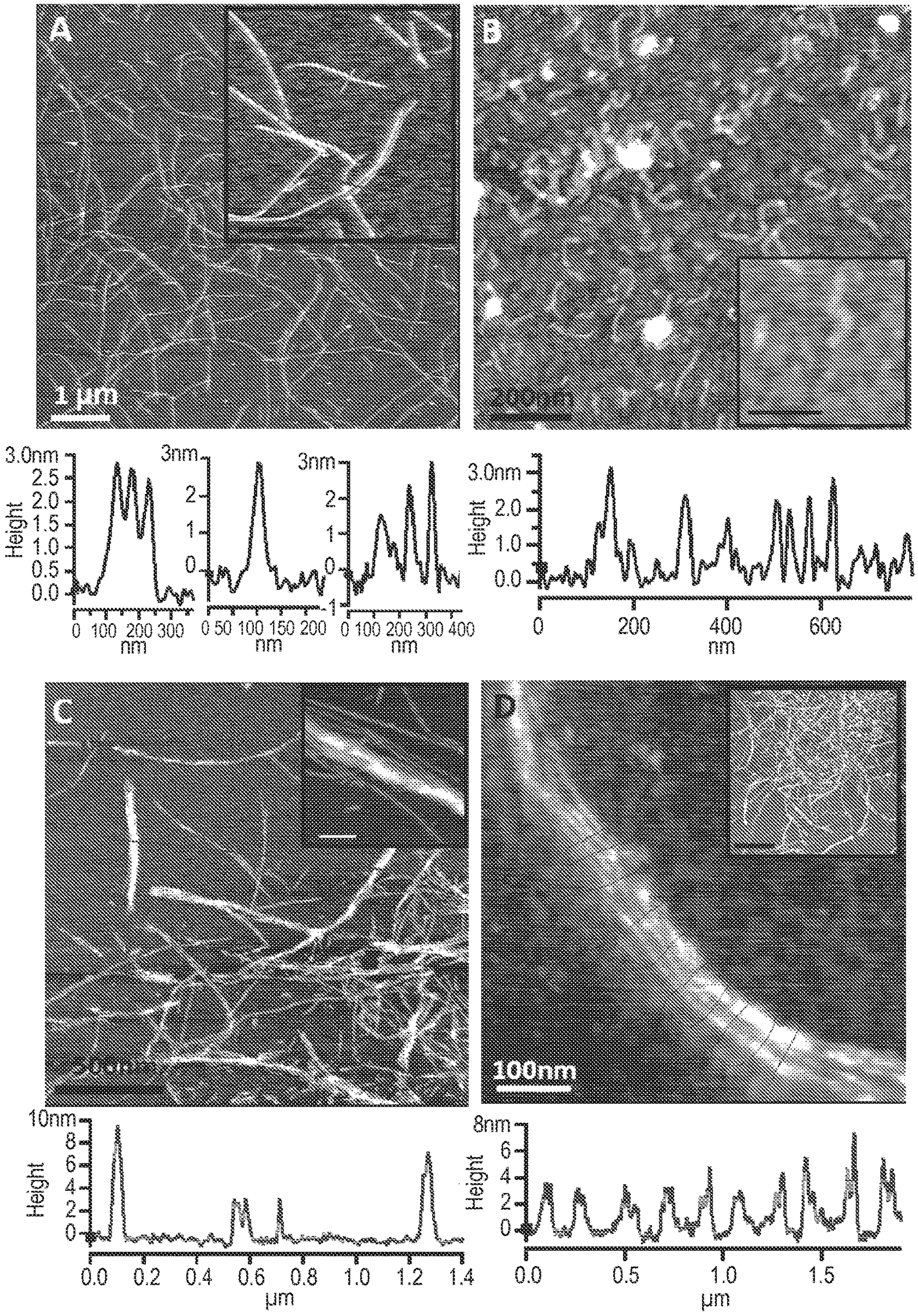
FIG. 10 shows AFM topography images of SBAFP-m1 and WT SBAFP. (A) SBAFP-m1 fibrils after 48 h incubation. Inset shows fibrils at higher magnification (bar=200 nm). Height profiles show that the height varies between 1.5 and 3.0 nm. (B) AFM image of WT SBAFP. Elongated structures and protein aggregates (indicated by red arrows) are present. The inset shows a higher magnification image (bar for insets=50 nm). Height profiles show that the heights of fibril-like structures are 2.0-3.0 nm. (C) Mature, three-week-old SBAFP-m1 fibrils. Red arrowheads indicate lateral assembly of SBAFP-m1 fibrils. Height profiles show variable (3, 8, and 10 nm) heights. The inset shows SBAFP-m1 fibrils in a parallel or antiparallel arrangement (bar=100 nm). (D) Internal structure of mature SBAFP-m1 fibril. Image indicates that mature fibrils contain at least approximately four 3 nm tall individual fibrils bundled together. The red line corresponds to the height profile plotted under the image. The inset shows randomly attached fibrils and fibril bundles of SBAFP-m1 (bar=2 μm).

The formation of fibers by SBAFP-m1 was analyzed after 48 h and 3 weeks of incubation at 37° C. After 48 h at 37° C., the proteins assembled into fibers, as revealed by AFM imaging (FIG. 10A). These fibers exhibit no branching or bundling and their lengths measure ~1-7 μm. The expansion (FIG. 10A inset) allows an accurate height determination of 1.5-3 nm, but predominantly between 2.5 and 3 nm. In contrast to SBAFP-m1, WT SBAFP does not yield well-defined fibrils under similar conditions. Instead, it forms arch shaped assemblies (40-150 nm in length), and amorphous aggregates (see red arrows in FIG. 10B). The height of the WT SBAFP monomers is 1 nm (see FIG. 10B inset).

Extended (e.g. 3 week) incubation at 37° C. leads to bundles of fibrils in the case of SBAFP-m1, as shown in FIG. 10C. The expanded view shows that the long axes of the fibrils are parallel to each other within each bundle (FIG. 10C inset and FIG. 10D) although the fibrils themselves, in the sense of N-to-C terminal may be parallel or antiparallel. The number of fibrils in each bundle varies from ~2-4 as shown on FIG. 10D. The overall height of the bundle varies from 6-10 nm, depending on the number of component fibers. The inset of FIG. 10C shows the number of individual SBAFP-m1 fibrils and overall diameter of a typical bundle. After 3 weeks of incubation at 37° C., SBAFP-m1 also forms random, haystack-like aggregates along with fibrils and bundles as shown in FIG. 10D.

Figure 11:
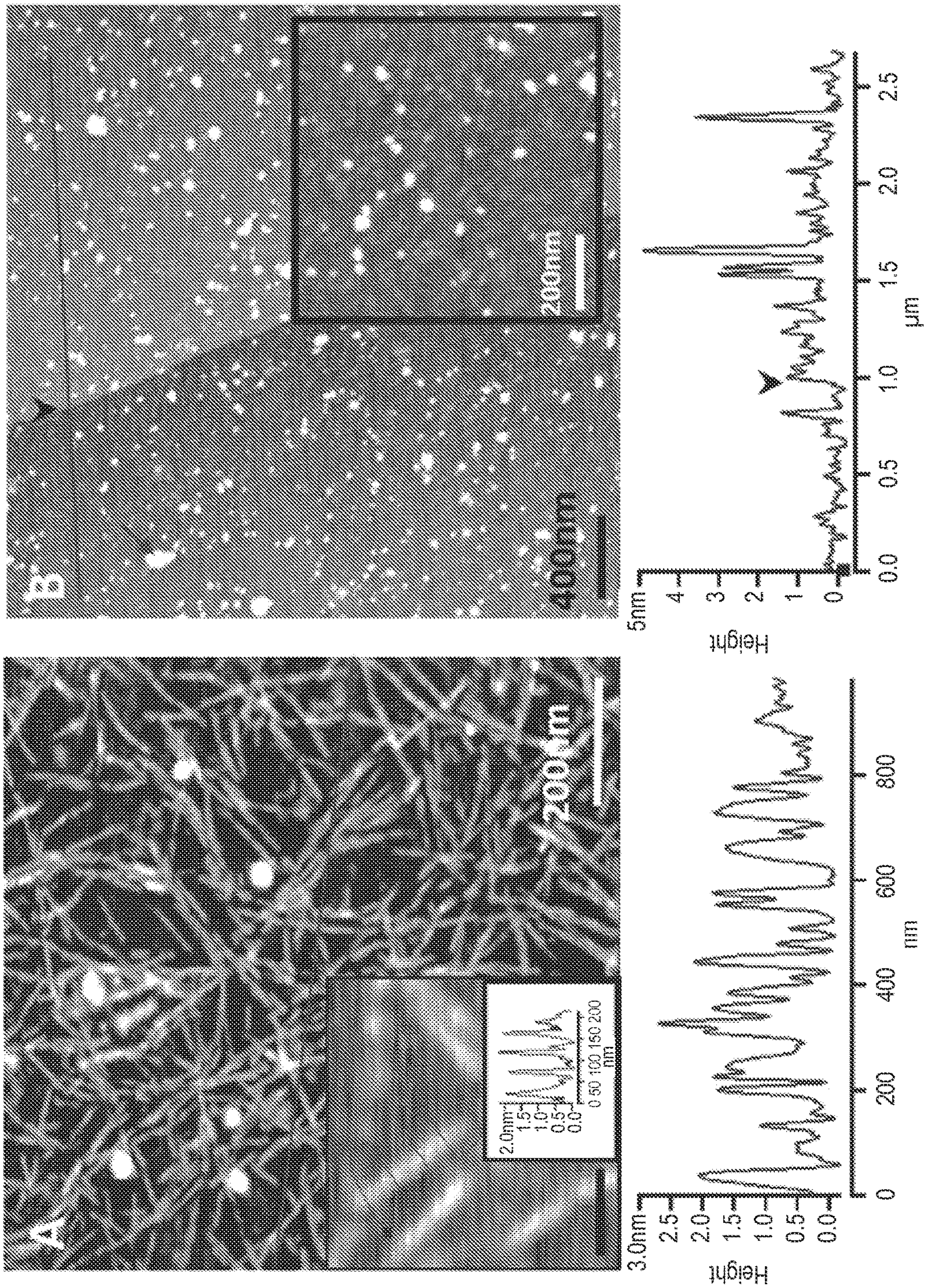
FIG. 11 shows AFM topography images of RGAFP-m1 and RGAFP on poly-L-Lysine coated mica(0001) surfaces. (A) A 1 μm×1 μm AFM image of RGAFP-m1. The red line corresponds to the height profile under the image. The height of RGAFP fibrils is around 2.0 nm. Tall features (indicated by red arrows) are likely aggregates of RGAFP-m1 monomers. The inset shows the height profile for a single fibril (bar=40 nm). (B) 3 m×3 μm AFM image of WT RGAFP. The red line corresponds to the height profile under the image. The inset shows a higher magnification, with individual bright features clearly shown. The red line indicated by the black arrow is a single layer step of mica(0001) with a known height of 1 nm.

AFM images of RGAFP-m1 samples were taken after three days incubation at 37° C. FIG. 11A shows high coverage of RGAFP-m1 fibrils. These fibrils are unbranched and very uniform in size, with height of 1.5-2.0 nm, and length of 150-400 nm. In contrast, no fibrillar structures were observed under the same condition using WT RGAFP, as shown in FIG. 11B. The bright features in AFM topographs measure 1-10 nm tall with various lateral dimensions, which is consistent with monomeric and aggregates of RGAFP monomers. The time-dependence of fibril and bundle formation is qualitatively consistent with known amyloid fibril formation kinetics.[51]

Kinetic Analysis

Figure 12:
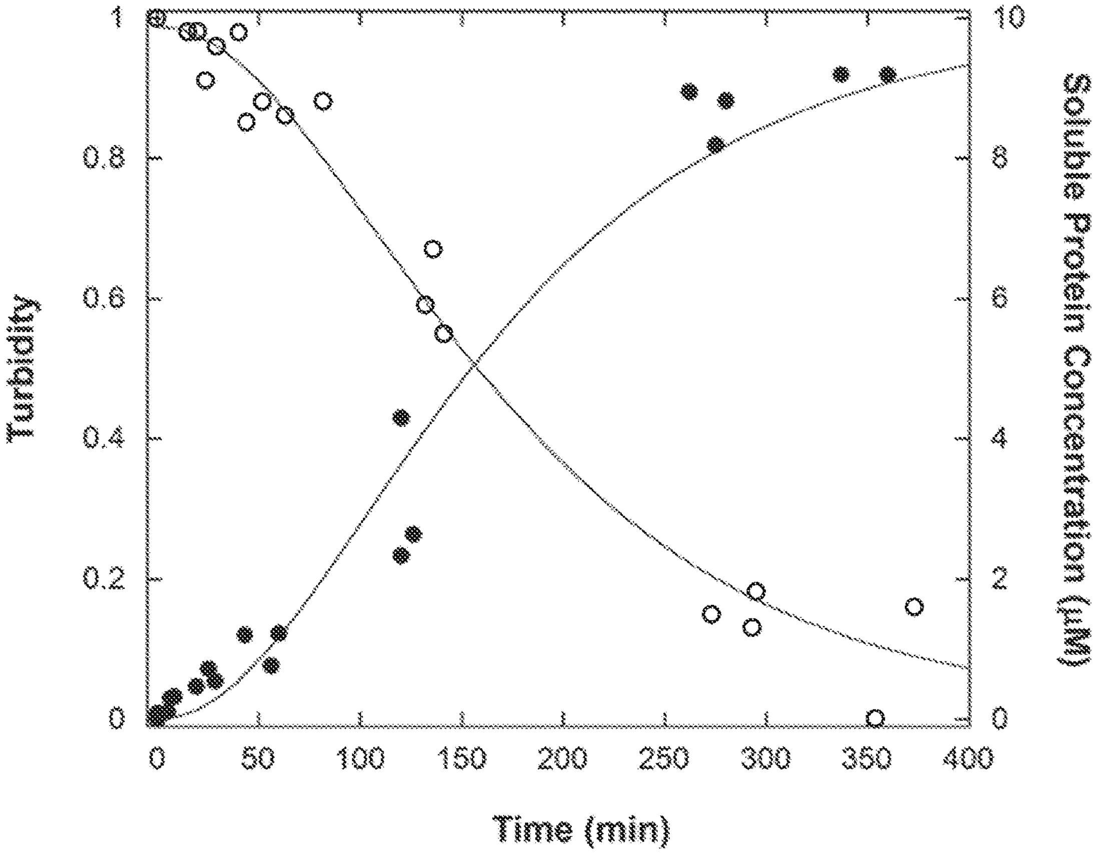
FIG. 12 shows kinetics of SBAFP-m1 fibril formation monitored by turbidity at 300 nm and total soluble protein in solution. A reaction mixture containing 10 μM SBAFP-m1 initially on ice was placed in a 37° C. incubator and shaken at 250 rpm to keep the sample mixed. At various times the reaction mixture was homogenized on a vortex mixer, a sample removed, and turbidity measured. The end-point turbidity is very close to 1 in these experiments. The sample was then centrifuged to remove insoluble protein and the soluble protein concentration measured. The data are a combination of three independent experiments and were fitted to Eq. 1. The forward rate constant for polymerization calculated from both types of data is 14±1 $M^{-1}$ $s^{-1}$.

The kinetics of fibril formation were followed for SBAFP-m1. DLS measurements on samples at 4° C. before the initiation of polymerization at 37° C. show the monomer as the only species present. Within 10 min of incubation at 37° C. the monomer is completely gone and replaced by larger species. The formation of large polymers was monitored by turbidity at 300 nm. A time course is presented in FIG. 12. A lag phase is indicated by the data, and a simple exponential model gives a poor fit. The data were analyzed within the framework presented by Ferrone.[52] Considering the 12 rung cross-β structure of SBAFP-m1, we assumed that the critical nucleus size is 1 so that the initial concentration of polymerization nuclei is equal to the initial concentration of protein. This leads to a simplified expression for the polymerization kinetics, given in Eq. 1, $$y=1-\mathrm{sech}(k_+\cdot M_0\cdot t) \quad (1)$$

where $k_+$ is the effective forward rate constant for polymerization, $M_0$ is the initial concentration of monomers, and t is time. This equation results from a new analytic solution to the Ferrone nucleated linear polymerization equations,[52] the full details of which will be presented elsewhere. By effective $k_+$ value here, we mean that we are not explicitly accounting for nucleation effects such as the need for a different, rare monomer conformation to nucleate fibrils as has been argued for PolyQ aggregation.[53]

Fitting the turbidity data to Eq. 1 (FIG. 12) gives a value of 14±1 $M^{-1}$ $s^{-1}$ for the rate constant, while fitting to ThT time course data (not shown) gives a value of 42±7 $M^{-1}$ $s^{-1}$. These effective values for $k_+$ are rapid compared to those measured for other cross-β fibril formation reactions. In particular, effective $k_+$ values from the literature are: 0.3 $M^{-1}$ $s^{-1}$ for insulin,[54] 3.3 $M^{-1}$ $s^{-1}$ for WT $PrP^{Sc}$ (prion) elongation in mice (assuming a concentration of $PrP^{C}$ in mice brain tissues),[55] 0.034, 0.3, and 1.4 $M^{-1}$ $s^{-1}$ for PolyQ polymers with 28, 36, 47 glutamines,[56] respectively, and 0.14, 0.58, 1.5, 6.9 $M^{-1}$ $s^{-1}$ for the spider silk amyloid peptide constructs eADF4(C2), eADF4(C4), eADF4(C8) and eADF4 (C16), respectively.[57] While a critical nucleus for aggregation of 1 was determined for the PolyQ case,[56] it is unknown in the others, and assumed to be 2 for insulin.[54] Nonetheless, it is apparent that despite the large size of the SBAFP monomers, the fact that they have preformed β-sheet structure affords much more rapid aggregation than other amyloids, particularly in the short time limit where aggregation goes generically as $k_+^{2}$.[52]

The fit assumes the turbidity is proportional to the total mass of polymer, which is a reasonable assumption provided that the fibril lengths exceed the wavelength of light (300 nm here).[58] This may break down in detail at short times in our experiments. We also note that our effective $k_+$ values fall many orders of magnitude below the Smoluchowski diffusion limit $k_D$ of about $10^9$ $M^{-1}$ $s^{-1}$,[59] a point noted before for polyQ aggregation.[53] In our case it is unlikely that this arises from a small probability nucleation complex as argued for PolyQ, since the monomer form appears highly stable on its own in simulations and experimentally in solution. It is possible for anisotropic geometric constraints to significantly reduce $k_+$, a point we shall explore in future work.

In preliminary experiments, we find that polymerization under identical conditions except that NaCl is added to 1 M final concentration occurs approximately 3-fold slower. When fibrils are harvested from polymerization reactions by centrifugation and resuspended in fresh buffer at 60° C., approximately 30% of the initial turbidity is lost in 1.5 h, after which it is stable over time. Similar experiments show that approximately 5% of the initial turbidity is lost when fibrils are resuspended in buffer containing 80% ethanol in 1.5 h, after which it is stable over time.

CONCLUSIONS

In conclusion, we have shown that two monomeric wild type antifreeze BSPs (from Spruce Budworm and Ryegrass) can be engineered to polymerize into amyloid fibrils as evidenced by CD, DLS, ThT fluorescence and AFM imaging, with the expected height profiles observed in AFM. To our knowledge, this is the first confirmation of amyloid formation from large BSP monomers, albeit in a synthetic context, despite the extant speculation that BSP structures should arise for known wild type amyloidogenic proteins[60-63] (we refer here to large BSPs with tightly packed interiors, although the Het-S fungal prion is known to form a more open β-solenoid amyloid structure[64]).

The evidence provided here demonstrates the applicability of these BSPs with extraordinary geometries for precision nanoscale applications such as templating nanoparticles for functional devices, enzyme arrays, peptide arrays for regenerative medicine, etc. Recently, enzymatic[65] and charge transfer[66] activity for peptide-based amyloids has been demonstrated. The larger and more readily manipulated BSPs employed here hold greater promise for tailor-made nanoscale templates with precisely spatially defined functionalization on the 2-10 nm scale.

It is understood that the examples and embodiments described herein are for illustrative purposes only and that various modifications or changes in light thereof will be suggested to persons skilled in the art and are to be included within the spirit and purview of this application and scope of the appended claims. All publications, patent Database Accessions, patents, and patent applications cited herein are hereby incorporated by reference in their entirety for all purposes.

REFERENCES

1. Olmsted, J. B.; Borisy, G. G. Microtubules. Annu. Rev. Biochem. 1973, 42, 507-540.
2. Zhang, S. G. Fabrication of Novel Biomaterials Through Molecular Self-assembly. Nat. Biotechnol. 2003, 21, 1171-1178.
3. Sara, M.; Sleytr, U. B. Crystalline Bacterial Cell Surface Layers (S-layers): From Cell Structure to Biomimetics. Prog. Biophys. Mol. Biol. 1996, 65, 83-111.
4. Chiti, F.; Dobson, C. M. Protein Misfolding, Functional Amyloid, and Human Disease. Annu. Rev. Biochem. 2006, 75, 333-366.
5. Seeman, N. C. Nanomaterials Based on DNA. In Annu. Rev. Biochem., Kornberg, R. D.; Raetz, C. R. H.; Rothman, J. E.; Thorner, J. W., Eds. 2010; Vol. 79, pp 65-87.
6. Le, J. D.; Pinto, Y.; Seeman, N. C.; Musier-Forsyth, K.; Taton, T. A.; Kiehl, R. A. DNA-templated Self-assembly of Metallic Nanocomponent Arrays on a Surface. Nano Lett. 2004, 4, 2343-2347.
7. Sacca, B.; Meyer, R.; Erkelenz, M.; Kiko, K.; Arndt, A.; Schroeder, H.; Rabe, K. S.; Niemeyer, C. M. Orthogonal Protein Decoration of DNA Origami. Angew. Chem., Int. Ed. 2010, 49, 9378-9383.
8. Liu, J. F.; Uprety, B.; Gyawali, S.; Woolley, A. T.; Myung, N. V.; Harb, J. N. Fabrication of DNA-Templated Te and Bi2Te3 Nanowires by Galvanic Displacement. Langmuir 2013, 29, 11176-11184.
9. Castro, C. E.; Kilchherr, F.; Kim, D.-N.; Shiao, E. L.; Wauer, T.; Wortmann, P.; Bathe, M.; Dietz, H. A Primer to Scaffolded DNA Origami. Nat. Methods 2011, 8, 221-229.
10. Mao, C. B.; Solis, D. J.; Reiss, B. D.; Kottmann, S. T.; Sweeney, R. Y.; Hayhurst, A.; Georgiou, G.; Iverson, B.; Belcher, A. M. Virus-based Toolkit for the Directed Synthesis of Magnetic and Semiconducting Nanowires. Science 2004, 303, 213-217.
11. Lee, Y. J.; Belcher, A. M. Nanostructure Design of Amorphous FePO4 Facilitated by a Virus for 3 V Lithium Ion Battery Cathodes. J. Mater. Chem. 2011, 21, 1033-1039.
12. Barnhart. M. M.; Chapman, M. R. Curli Biogenesis and Function. Annu. Rev. Microbiol. 2006, 60, 131-147.
13. Si, K.; Choi, Y. B.; White-Grindley, E.; Majumdar, A.; Kandel. E. R. Aplysia CPEB Can Form Prion-like Multimers in Sensory Neurons that Contribute to Long-Term Facilitation. Cell 2010, 140, 421-U179.
14. Maji, S. K.; Perrin, M. H.; Sawaya, M. R.; Jessberger, S.; Vadodaria, K.; Rissman, R. A.; Singru. P. S.; Nilsson, K. P. R.; Simon, R.; Schubert, D.; al., e. Functional Amyloids As Natural Storage of Peptide Hormones in Pituitary Secretory Granules. Science 2009, 325, 328-332.
15. Knowles, T. P. J.; Smith, J. F.; Craig, A.; Dobson, C. M.; Welland, M. E. Spatial Persistence of Angular Correlations in Amyloid Fibrils. Phys. Rev. Lett. 2006, 96.
16. Knowles, T. P. J.; Buehler, M. J. Nanomechanics of Functional and Pathological Amyloid Materials. Nat. Nanotechnol. 2011, 6, 469-479.
17. Slotta, U.; Hess, S.; Spiess. K.; Stromer, T.; Serpell, L.; Scheibel, T. Spider Silk and Amyloid Fibrils: A Structural Comparison. Macromol. Biosci. 2007, 7, 183-188.
18. Sullan, R. M. A.; Gunari, N.; Tanur, A. E.; Yuri. C.; Dickinson, G. H.; Orihuela, B.; Rittschof. D.; Walker, G. C. Nanoscale Structures and Mechanics of Barnacle Cement. Biofouling 2009, 25, 263-275.
19. Scheibel, T.; Parthasarathy, R.; Sawicki, G.; Lin, X. M.; Jaeger, H.; Lindquist, S. L. Conducting Nanowires Built by Controlled Self-assembly of Amyloid Fibers and Selective Metal Deposition. Proc. Natl. Acad. Sci. U.S.A 2003, 100, 4527-4532.
20. Reches, M.; Gazit, E. Casting Metal Nanowires Within Discrete Self-assembled Peptide Nanotubes. Science 2003, 300, 625-627.
21. Sakai, H.; Watanabe, K.; Asanomi, Y.; Kobayashi, Y.; Chuman. Y.; Shi, L. H.; Masuda. T.; Wyttenbach, T.; Bowers, M. T.; Uosaki. K.; Sakaguchi, K. Formation of Functionalized Nanowires by Control of Self-Assembly Using Multiple Modified Amyloid Peptides. Adv. Funct. Mater. 2013, 23, 4881-4887.
22. Knowles, T. P. J.; Oppenheim, T. W.; Buell, A. K.; Chirgadze, D. Y.; Welland. M. E. Nanostructured Films from Hierarchical Self-assembly of Amyloidogenic Proteins. Nat. Nanotechnol. 2010, 5, 204-207.
23. Arora, A.; Ha, C.; Park, C. B. Insulin Amyloid Fibrillation at Above 100 degrees C.: New Insights into Protein Folding Under Extreme Temperatures. Protein Sci. 2004, 13, 2429-2436.

24. Baxa, U.; Ross, P. D.; Wickner, R. B.; Steven, A. C. The N-terminal Prion Domain of Ure2p Converts from an Unfolded to a Thermally Resistant Conformation Upon Filament Formation. J. Mol. Biol. 2004, 339, 259-264.
25. Kardos, J.; Micsonai, A.; Pal-Gabor, H.; Petrik, E.; Graf. L.; Kovacs, J.; Lee, Y. H.; Naiki, H.; Goto, Y. Reversible Heat-Induced Dissociation of beta(2)-Microglobulin Amyloid Fibrils. Biochemistry 2011, 50, 3211-3220.
26. Hammer, N. D.; Wang, X.; McGuffie, B. A.; Chapman, M. R. Amyloids: Friend or foe? Journal of Alzheimers Disease 2008, 13, 407-419.
27. Ryu, J.; Park, C. B. High Stability of Self-Assembled Peptide Nanowires Against Thermal, Chemical, and Proteolytic Attacks. Biotechnol. Bioeng. 2010, 105, 221-230.
28. Sunde, M.; Blake, C. The Structure of Amyloid Fibrils by Electron Microscopy and X-ray Diffraction. Adv. Protein Chem. 1997, 50, 123-159.
29. Wille, H.; Bian, W.; McDonald, M.; Kendall, A.; Colby, D. W.; Bloch, L.; Ollesch, J.; Borovinskiy, A. L.; Cohen. F. E.; Prusiner, S. B.; Stubbs, G. Natural and Synthetic Prion Structure from X-ray Fiber Diffraction. Proc. Natl. Acad. Sci. U.S.A 2009, 106, 16990-16995.
30. Buell, A. K.; Dhulesia, A.; Mossuto, M. F.; Cremades, N.; Kumita, J. R.; Dumoulin, M.; Welland, M. E.; Knowles. T. P. J.; Salvatella, X.; Dobson, C. M. Population of Nonnative States of Lysozyme Variants Drives Amyloid Fibril Formation. J. Am. Chem. Soc. 2011, 133, 7737-7743.
31. Graether, S. P.; Kuiper, M. J.; Gagne, S. M.; Walker, V. K.; Jia, Z. C.; Sykes, B. D.; Davies, P. L. beta-helix structure and ice-binding properties of a hyperactive antifreeze protein from an insect. Nature 2000, 406, 325-328.
32. Benbassat, A.; Bauer. K.; Chang. S. Y.; Myambo, K.; Boosman, A.; Chang, S. Processing of the Initiation Methionine from Proteins—Properties of the *Escherichia-Coli* Methionine Aminopeptidase and its Gene Structure. J. Bacteriol. 1987, 169, 751-757.
33. Gauthier, S. Y.; Kay, C. M.; Sykes. B. D.; Walker, V. K.; Davies, P. L. Disulfide Bond Mapping and Structural Characterization of Spruce Budworm Antifreeze Protein. Eur. J. Biochem. 1998, 258, 445-453.
34. Middleton. A. J.; Marshall, C. B.; Faucher, F.; Bar-Dolev, M.; Braslavsky, I.; Campbell, R. L.; Walker, V. K.; Davies, P. L. Antifreeze Protein from Freeze-Tolerant Grass Has a Beta-Roll Fold with an Irregularly Structured Ice-Binding Site. J. Mol. Biol. 2012, 416, 713-724.
35. Cooper, S.; Khatib, F.; Treuille, A.; Barbero, J.; Lee, J.; Beenen. M.; Leaver-Fay, A.; Baker, D.; Popovic, Z.; Players, F. Predicting Protein Structures with a Multiplayer Online Game. Nature 2010, 466, 756-760.
36. D. A. Case, T. A. D., T. E. Cheatham, III, C. L. Simmerling, J. Wang, R. E. Duke, R.; Luo, R. C. W., W. Zhang, K. M. Merz, B. Roberts, S. Hayik, A. Roitberg, G. Seabra; J. Swails, A. W. G., I. Kolossváry, K. F. Wong, F. Paesani, J. Vanicek, R. M. Wolf, J. Liu; X. Wu, S. R. B., T. Steinbrecher, H. Gohlke, Q. Cai, X. Ye, J. Wang, M.-J. Hsieh, G.; Cui, D. R. R., D. H. Mathews, M. G. Seetin, R. Salomon-Ferrer, C. Sagui, V. Babin, T.; Luchko, S. G., A. Kovalenko, and P. A. Kollman AMBER 12, University of California San Francisco. 2012.
37. Humphrey, W.; Dalke, A.; Schulten, K. VMD: Visual Molecular Dynamics. J. Mol. Graphics Modell. 1996, 14, 33-38.
38. Steinle, A.; Li, P.; Morris, D. L.; Groh, V.; Lanier, L.; Strong, R. K.; Spies, T. Interactions of human NKG2D with its ligands MICA, MICB, and homologs of the mouse RAE-1 protein family. Immunogenetics 2001, 52, 279-287.
39. Provencher, S. W.; Glockner, J. Estimation of Globular Protein Secondary Structure from Circular-dichroism. Biochemistry 1981, 20, 33-37.
40. Janes, R. W.; Wallace, B. A. Modern Techniques in Circular Dichroism and Synchrotron Radiation Circular Dichroism Spectroscopy. IOS Press: 2009.
41. Whitmore, L.; Wallace, B. A. Protein Secondary Structure Analyses from Circular Dichroism Spectroscopy: Methods and References Databases. Biopolymers 2007, 89, 392-400.
42. Sreerama, N.; Woody, R. W. Estimation of Protein Secondary Structure from Circular Dichroism Spectra: Comparison of CONTIN, SELCON, and CDSSTR Methods with an Expanded Reference Set. Anal. Biochem. 2000, 287, 252-260.
43. Greenfield, N. J. Using Circular Dichroism Spectra to Estimate Protein Secondary Structure. Nat. Protoc. 2006, 1, 2876-2890.
44. Vassar, P. S.; Culling, C. F. A. Fluorescent Stains, with Special Reference to Amyloid and Connective Tissues. Arch. Pathol. 1959, 68, 487-498.
45. Levine. H. Thioflavine-T Interaction with Synthetic Alzheimers-disease Beta-amyloid Peptides—Detection of Amyloid Aggregation in Solution. Protein Sci. 1993, 2, 404-410.
46. Biancalana, M.; Koide, S. Molecular Mechanism of Thioflavin-T Binding to Amyloid Fibrils. Biochim. Biophys. Acta, Proteins Proteomics 2010, 1804, 1405-1412.
47. LeVine, H. Quantification of Beta-sheet Amyloid Fibril Structures with Thioflavin-T. Amyloid, Prions, and Other Protein Aggregates 1999, 309, 274-284.
48. Nielsen, L.; Khurana, R.; Coats, A.; Frokjaer, S.; Brange, J.; Vyas, S.; Uversky, V. N.; Fink, A. L. Effect of Environmental Factors on the Kinetics of Insulin Fibril Formation: Elucidation of the Molecular Mechanism. Biochemistry 2001, 40, 6036-6046.
49. Ionescu-Zanetti, C.; Khurana, R.; Gillespie, J. R.; Petrick, J. S.; Trabachino. L. C.; Minert, L. J.; Carter, S. A.; Fink, A. L. Monitoring the Assembly of Ig Light-chain Amyloid Fibrils by Atomic Force Microscopy. Proc Natl Acad Sci USA 1999, 96, 13175-13179.
50. Kusumoto, Y.; Lomakin, A.; Teplow, D. B.; Benedek, G. B. Temperature Dependence of Amyloid Beta-protein Fibrillization. Proc Natl Acad Sci USA 1998, 95, 12277-12282.
51. Harrison, R. S.; Sharpe, P. C.; Singh. Y.; Fairlie. D. P. Amyloid Peptides and Proteins in Review. Rev. Physiol., Biochem. Pharmacol. 2007, 159, 1-77.
52. Ferrone, F. Analysis of Protein Aggregation Kinetics. Methods Enzymol. 1999, 309, 256-274.
53. Bhattacharyya, A. M.; Thakur, A. K.; Wetzel, R. Polyglutamine aggregation nucleation: Thermodynamics of a highly unfavorable protein folding reaction. Proceedings of the National Academy of Sciences of the United States of America 2005, 102, 15400-15405.
54. Knowles, T. P. J.; Waudby, C. A.; Devlin, G. L.; Cohen, S. I. A.; Aguzzi, A.; Vendruscolo, M.; Terentjev, E. M.; Welland, M. E.; Dobson, C. M. An Analytical Solution to the Kinetics of Breakable Filament Assembly. Science 2009, 326, 1533-1537.
55. Cox, D. L.; Singh, R. R. P.; Yang, S. C. Prion Disease: Exponential Growth Requires Membrane Binding. Biophys. J. 2006, 90, L77-L79.

56. Chen, S. M.; Ferrone. F. A.; Wetzel, R. Huntington's Disease Age-of-onset Linked to Polyglutamine Aggregation Nucleation. Proc Natl Acad Sci USA 2002, 99, 11884-11889.

57. Humenik, M., Magdeburg, M., and Scheibel, T. Influence of Repeat Numbers on Self-assembly Rates of Repetitive Recombinant Spider Silk Proteins. J. Struct. Biol. 2014, 186, 431-437.

58. Berne, B. J. Interpretation of the Light Scattering from Long Rods J Mol Biol 1974, 89, 755-758.

59. Northrup, S. H.; Erickson, H. P. Kinetics of Protein-Protein Association Explained by Brownian Dynamics Computer-simulation. Proc Natl Acad Sci USA 1992, 89, 3338-3342.

60. Perutz, M. F.; Finch, J. T.; Berriman. J.; Lesk, A. Amyloid Fibers are Water-filled Nanotubes. Proc Natl Acad Sci USA 2002, 99, 5591-5595.

61. Govaerts, C.; Wille, H.; Prusiner, S. B.; Cohen, F. E. Evidence for Assembly of Prions with Left-handed Beta 3-helices into Trimers. Proc Natl Acad Sci USA 2004, 101, 8342-8347.

62. Stork, M.; Giese, A.; Kretzschmar, H. A.; Tavan, P. Molecular Dynamics Simulations Indicate a Possible Role of Parallel Beta-helices in Seeded Aggregation of Poly-Gln. Biophys J 2005, 88, 2442-2451.

63. Kunes, K. C.; Clark. S. C.; Cox, D. L.; Singh, R. R. P. Left Handed Beta-helix Models for Mammalian Prion Fibrils. Prion 2008, 2, 81-90.

64. Wasmer, C.; Lange, A.; Van Melckebeke, H.; Siemer, A. B.; Rick, R.; Meier, B. H. Amyloid Fibrils of the HET-s (218-289) Prion Form a Beta Solenoid with a Triangular Hydrophobic Core. Science 2008, 319, 1523-1526.

65. Rufo, C. M.; Moroz, Y. S.; Moroz, O. V.; Stohr, J.; Smith, T. A.; Hu, X. Z.; DeGrado, W. F.; Korendovych, I. V. Short Peptides Self-assemble to Produce Catalytic Amyloids. Nat. Chem. 2014, 6, 303-309.

66. Ivnitski, D.; Amit, M.; Rubinov. B.; Cohen-Luria, R.; Ashkenasy, N.; Ashkenasy, G. Introducing Charge Transfer Functionality into Prebiotically Relevant Beta-sheet Peptide Fibrils. Chem. Commun. (Cambridge. U. K.) 2014, 50, 6733-6736.

67. Khurana, R.; Coleman, C.; Ionescu-Zanetti, C.; Carter, S. A.; Krishna, V.; Grover. R. K.; Roy. R.; Singh. S. Mechanism of Thioflavin-T Binding to Amyloid Fibrils. J. Struct. Biol. 2005, 151, 229-238.

68. Buchko, G. W.; Ni, S. S.; Robinson, H.; Welsh, E. A.; Pakrasi, H. B.; Kennedy, M. A. Characterization of Two Potentially Universal Turn Motifs that Shape the Repeated Five-residues Fold—Crystal Structure of a Lumenal Pentapeptide Repeat Protein from Cyanothece 51142. Protein Sci. 2006, 15, 2579-2595.

69. Ni, S. S.; Sheldrick, G. M.; Benning, M. M.; Kennedy, M. A. The 2 Angstrom Resolution Crystal Structure of HetL, a Pentapeptide Repeat Protein Involved in Regulation of Heterocyst Differentiation in the *Cyanobacterium Nostoc* Sp Strain PCC 7120. J. Struct. Biol. 2009, 165, 47-52.

70. Pentelute, B. L.; Gates, Z. P.; Tereshko, V.; Dashnau, J. L.; Vanderkooi, J. M.; Kossiakoff, A. A.; Kent, S. B. H. X-ray Structure of Snow Flea Antifreeze Protein Determined by Racemic Crystallization of Synthetic Protein Enantiomers. J. Am. Chem. Soc. 2008, 130, 9695-9701.

71. Lauersen, K. J.; Brown, A.; Middleton, A.; Davies, P. L.; Walker, V. K. Expression and Characterization of an Antifreeze Protein from the Perennial Rye Grass, Lolium Perenne. Cryobiology 2011, 62, 194-201.

72. Benach, J., Chen, Y., Vorobiev, S. M., Seetharaman, J., Ho, C. K., Janjua, H., Conover, K., Ma, L-C., Xiao, R., et al. Crystal Structure of ydcK from *Salmonella Cholerae* at 2.38 A Resolution, on the world wide web at pdb.org/pdb/explore/explore.do?structureId=2PIG.

73. Leinala, E. K.; Davies, P. L.; Doucet, D.; Tyshenko, M. G.; Walker, V. K.; Jia, Z. C. A Beta-helical Antifreeze Protein Isoform with Increased Activity—Structural and Functional Insights. J. Biol. Chem. 2002, 277, 33349-33352.

INFORMAL SEQUENCE LISTING

SEQ ID NO: 1
SBAFP-m1 amino acid sequence

SEQ ID NO: 2
SBAFP-m1 amino acid sequence

Exemplary BSPs:
Chain A, Crystal Structure Of A Lumenal Pentapeptide Repeat Protein From *Cyanothece* Sp 51142 At 2.3 Angstrom Resolution. Tetragonal Crystal Form
a. PDB:2G0Y_A

```
  1    mhhhhhhssg lvprgsgmke taakferqhm dspdlgtddd dkamamvtgs sasyedvkli
 61    gedfsgkslt yaqftnadlt dsnfseadlr gavfngsali gadlhgadlt nglayltsfk
121    gadltnavlt eaimmrtkfd dakitgadfs lavldvyevd klcdradgvn pktgvstres
181    lrcq
```

1. Chain X, The 2.0 Angstrom Resolution Crystal Structure Of Hetl, A Pentapeptide Repeat Protein Involved In Heterocyst Differentiation Regulation From The *Cyanobactcrium Nostoc* Sp. Strain Pcc 7120
b. PDB:3DU1_X

```
  1    mgsshhhhhh ssglvprgsh mnvgeilrhy aagkrnfqhi nlqeieltna sltgadlsya
 61    dlrqtrlgks nfshtclrea dlseailwgi dlseadlyra ilreadltga klvktrleea
121    nlikaslcga nlnsanlsrc llfqadlrps snqrtdlgyv lltgadlsya dlraaslhha
181    nldgaklcra nfgrtiqwgn laadlsgasl qgadlsyanl esailrkanl qgadltgail
241    kdaelkgaim pdgsihd
```

2. Chain A, Crystal Structure Of Recombinant Human Alpha *Lactalbumin*
c. PDB:3B0I_A

```
  1    mkqftkcels qllkdidgyg gialpelict mfhtsgydtq aivenneste yglfqisnkl
 61    wckssqvpqs rnicdiscdk flddditddi mcakkildik gidywlahka lctekleqwl
121    cekl
```

-continued

INFORMAL SEQUENCE LISTING

3. Chain B, Crystal Structure Of An Ice-Binding Protein From The Perennial Ryegrass, *Lolium Perenne*
d. PDB:3ULT_B

```
  1    mdeqpntisg snntvrsgsk nvlagndntv isgdnnsvsg snntvvsgnd ntvtgsnhvv
 61    sgtnhivtdn nnnvsgndnn vsgsfhtvsg ghntvsgsnn tvsgsnhvvs gsnkvvtdaa
121    klaaalehhh hhh
```

4. Chain A, Crystal Structure Of An Ice-Binding Protein From The Perennial Ryegrass, *Lolium Perenne*
e. PDB:3ULT_A

```
  1    mdeqpntisg snntvrsgsk nvlagndntv lsgdnnsvsg snntwsgnd ntvtgenhw
 61    sgtnhivtdn nnnvsgndnn vsgsfhtvsg ghntvsgsnn tvsgsnhws gsnkwtdaa
121    klaaalehhh hhh
```

5. Chain B, Crystal Structure Of Ydck From *Salmonella Cholerae* At 2.38 A Resolution. Northeast Structural Genomics Target Scr6
f. PDB:2PIG_B

```
  1    xtkyrlsegp raftyqvdge kksvllrqvi avtdfndvka gtsggwvdad nvlsqqgdcw
 61    iydenaxafa gteitgnari tqpctlynnv rigdnvwidr adisdgaris dnvtiqsssv
121    reecaiygda rvlnqseila iqglthehaq ilqiydratv nhsrivhqvq lygnatitha
181    fiehraevfd faliegdkdn nvwicdcakv ygharviagt eedaiptlry ssqvaehali
241    egncvlkhhv lvgghaevrg gpillddrvl ieghaciqge ilierqveis graaviafdd
301    ntihlrgpkv ingedritrt plvgsllehh hhhh
```

6. Chain A, Crystal Structure Of Ydck From *Salmonella Cholerae* At 2.38 A Resolution. Northeast Structural Genomics Target Scr6
g. PDB:2PIG_A

```
  1    xtkyrlsegp raftyqvdge kksvllrqvi avtdfndvka gtsggwvdad nvlsqqgdcw
 61    iydenaxafa gteitgnari tqpctlynnv rigdnvwidr adisdgaris dnvtiqsssv
121    reecaiygda rvlnqseila iqglthehaq ilqiydratv nhsrivhqvq lygnatitha
181    fiehraevfd faliegdkdn nvwicdcakv ygharviagt eedaiptlry ssqvaehali
241    egncvlkhhv lvgghaevrg gpillddrvl ieghaciqge ilierqveis graaviafdd
301    ntihlrgpkv ingedritrt plvgsllehh hhhh
```

7. Chain A, *Choristoncura Fumiferana* (Spruce Budworm) Antifreeze Protein Isoform 501
h. PDB:1M8N_A

```
  1    dgtcvntnsq itansqcvks tatncyidns qlvdtsictr sqysdanvkk svttdcnidk
 61    sqvylttctg sqyngiyirs stttgtsisg pgcsistcti trgvatpaaa ckisgcslsa
121    m
```

8. Chain B, *Choristoneura Fumiferana* (Spruce Budworm) Antifreeze Protein Isoform 501
i. PDB:1M8N_B

```
  1    dgtcvntnsq itansqcvks tatncyidns qlvdtsictr sqysdanvkk svttdcnidk
 61    sqvylttctg sqyngiyirs stttgtsisg pgcsistcti trgvatpaaa ckisgcslsa
121    m
```

9. Chain C, *Choristoneura Fumiferana* (Spruce Budworm) Antifreeze Protein Isoform 501
j. PDB:1M8N_C

```
  1    dgtcvntnsq itansqcvks tatncyidns qlvdtsictr sqysdanvkk svttdcnidk
 61    sqvylttctg sqyngiyirs stttgtsisg pgcsistcti trgvatpaaa ckisgcslsa
121    m
```

10. Chain D, *Choristoneura Fumiferana* (Spruce Budworm) Antifreeze Protein Isoform 501
k. PDB:1M8N_D

```
  1    dgtcvntnsq itansqcvks tatncyidns qlvdtsictr sqysdanvkk svttdcnidk
 61    sqvylttctg sqyngiyirs stttgtsisg pgcsistcti trgvatpaaa ckisgcslsa
121    m
```

What is claimed is:

1. An amyloid fibril comprising a plurality of modified β solenoid protein (mBSP) monomers, wherein each mBSP monomer is modified from a non-amyloidogenic wild-type β solenoid protein (WT-BSP) to remove an end cap that prevents amyloid aggregation and thereby allow for controlled amyloid self-assembly.

2. The amyloid fibril of claim 1, wherein the mBSP monomers are derived from an antifreeze protein.

3. The amyloid fibril of claim 2, wherein the antifreeze protein is a spruce budworm antifreeze protein.

4. The amyloid fibril of claim 3, wherein the mBSP has the sequence shown in SEQ ID NO: 1.

5. The amyloid fibril of claim 1, wherein the antifreeze protein is a rye grass antifreeze protein.

6. The amyloid fibril of claim 5, wherein the mBSP has the sequence shown in SEQ ID NO: 2.

7. The amyloid fibril of claim 1, that is modified to include at least one amino acid residue that promotes attachment of the fibril to a solid support, a nanoparticle, a biological molecule, or a second amyloid fibril.

* * * * *

SEQUENCE LISTING

<160> NUMBER OF SEQ ID NOS: 15

<210> SEQ ID NO 1
<211> LENGTH: 91
<212> TYPE: PRT
<213> ORGANISM: Artificial Sequence
<220> FEATURE:
<223> OTHER INFORMATION: synthetic peptide SBAFP-m1

<400> SEQUENCE: 1

```
Ala Ser Arg Ile Thr Asn Ser Gln Ile Val Lys Ser Glu Ala Thr Asn
1               5                   10                  15
```

Ser Asp Ile Asn Asn Ser Gln Leu Val Asp Ser Ile Ser Thr Arg Ser
20 25 30

Gln Tyr Ser Asp Ala Asn Val Lys Lys Ser Val Thr Thr Asp Ser Asn
35 40 45

Ile Asp Lys Ser Gln Val Tyr Leu Thr Thr Ser Thr Gly Ser Gln Tyr
50 55 60

Asn Gly Ile Tyr Ile Arg Ser Ser Asp Thr Thr Gly Ser Glu Ile Ser
65 70 75 80

Gly Ser Ser Ile Ser Thr Ser Arg Ile Thr Ile
85 90

<210> SEQ ID NO 2
<211> LENGTH: 111
<212> TYPE: PRT
<213> ORGANISM: Artificial Sequence
<220> FEATURE:
<223> OTHER INFORMATION: synthetic peptide RGAFP-m1

<400> SEQUENCE: 2

Ala Asn Asp Ile Asp Gly Thr Asn Asn Glu Val Asp Gly Ser Glu Asn
1 5 10 15

Val Leu Ala Gly Asn Asp Asn Thr Val Ser Gly Asp Asn Asn Ser Val
20 25 30

Ser Gly Ser Asn Asn Thr Val Ser Gly Asn Asp Asn Thr Val Thr Gly
35 40 45

Ser Asn Met Val Val Ser Gly Thr Asn Met Ile Val Thr Asp Asn Asn
50 55 60

Asn Asn Val Ser Gly Asn Asp Asn Asn Val Ser Gly Ser Phe Met Thr
65 70 75 80

Val Ser Gly Gly Met Asn Thr Val Ser Gly Ser Asn Asn Thr Val Ser
85 90 95

Gly Lys Arg Met Arg Val Gln Gly Thr Asn Asn Arg Val Thr Asp
100 105 110

<210> SEQ ID NO 3
<211> LENGTH: 100
<212> TYPE: PRT
<213> ORGANISM: Choristoneura fumiferana

<400> SEQUENCE: 3

Asp Gly Thr Cys Val Asn Thr Asn Ser Gln Ile Thr Ala Asn Ser Gln
1 5 10 15

Cys Val Lys Ser Thr Ala Thr Asn Cys Tyr Ile Asp Asn Ser Gln Leu
20 25 30

Val Asp Thr Ser Ile Cys Thr Arg Ser Gln Tyr Ser Asp Ala Asn Val
35 40 45

Lys Lys Ser Val Thr Thr Asp Cys Asn Ile Asp Lys Ser Gln Val Tyr
50 55 60

Leu Thr Thr Cys Thr Gly Ser Gln Tyr Asn Gly Ile Tyr Ile Arg Ser
65 70 75 80

Ser Thr Thr Thr Gly Thr Ser Ile Ser Gly Pro Gly Cys Ser Ile Ser
85 90 95

Thr Cys Thr Ile
100

<210> SEQ ID NO 4
<211> LENGTH: 114

-continued

<212> TYPE: PRT
<213> ORGANISM: Lolium perenne

<400> SEQUENCE: 4

```
Pro Asn Thr Ile Ser Gly Ser Asn Asn Thr Val Arg Ser Gly Ser Lys
1               5                   10                  15

Asn Val Leu Ala Gly Asn Asp Asn Thr Val Ile Ser Gly Asp Asn Asn
            20                  25                  30

Ser Val Ser Gly Ser Asn Asn Thr Val Val Ser Gly Asn Asp Asn Thr
        35                  40                  45

Val Thr Gly Ser Asn His Val Val Ser Gly Thr Asn His Ile Val Thr
    50                  55                  60

Asp Asn Asn Asn Asn Val Ser Gly Asn Asp Asn Asn Val Ser Gly Ser
65                  70                  75                  80

Phe His Thr Val Ser Gly Gly His Asn Thr Val Ser Gly Ser Asn Asn
                85                  90                  95

Thr Val Ser Gly Ser Asn His Val Val Ser Gly Ser Asn Lys Val Val
            100                 105                 110

Thr Asp
```

<210> SEQ ID NO 5
<211> LENGTH: 184
<212> TYPE: PRT
<213> ORGANISM: Cyanothece ATCC51142

<400> SEQUENCE: 5

```
Met His His His His His His Ser Ser Gly Leu Val Pro Arg Gly Ser
1               5                   10                  15

Gly Met Lys Glu Thr Ala Ala Lys Phe Glu Arg Gln His Met Asp Ser
            20                  25                  30

Pro Asp Leu Gly Thr Asp Asp Asp Asp Lys Ala Met Ala Met Val Thr
        35                  40                  45

Gly Ser Ser Ala Ser Tyr Glu Asp Val Lys Leu Ile Gly Glu Asp Phe
    50                  55                  60

Ser Gly Lys Ser Leu Thr Tyr Ala Gln Phe Thr Asn Ala Asp Leu Thr
65                  70                  75                  80

Asp Ser Asn Phe Ser Glu Ala Asp Leu Arg Gly Ala Val Phe Asn Gly
                85                  90                  95

Ser Ala Leu Ile Gly Ala Asp Leu His Gly Ala Asp Leu Thr Asn Gly
            100                 105                 110

Leu Ala Tyr Leu Thr Ser Phe Lys Gly Ala Asp Leu Thr Asn Ala Val
        115                 120                 125

Leu Thr Glu Ala Ile Met Met Arg Thr Lys Phe Asp Asp Ala Lys Ile
    130                 135                 140

Thr Gly Ala Asp Phe Ser Leu Ala Val Leu Asp Val Tyr Glu Val Asp
145                 150                 155                 160

Lys Leu Cys Asp Arg Ala Asp Gly Val Asn Pro Lys Thr Gly Val Ser
                165                 170                 175

Thr Arg Glu Ser Leu Arg Cys Gln
            180
```

<210> SEQ ID NO 6
<211> LENGTH: 257
<212> TYPE: PRT
<213> ORGANISM: Nostoc sp. PCC7120

<400> SEQUENCE: 6

```
Met Gly Ser Ser His His His His His His Ser Ser Gly Leu Val Pro
1               5                   10                  15

Arg Gly Ser His Met Asn Val Gly Glu Ile Leu Arg His Tyr Ala Ala
            20                  25                  30

Gly Lys Arg Asn Phe Gln His Ile Asn Leu Gln Glu Ile Glu Leu Thr
        35                  40                  45

Asn Ala Ser Leu Thr Gly Ala Asp Leu Ser Tyr Ala Asp Leu Arg Gln
    50                  55                  60

Thr Arg Leu Gly Lys Ser Asn Phe Ser His Thr Cys Leu Arg Glu Ala
65                  70                  75                  80

Asp Leu Ser Glu Ala Ile Leu Trp Gly Ile Asp Leu Ser Glu Ala Asp
                85                  90                  95

Leu Tyr Arg Ala Ile Leu Arg Glu Ala Asp Leu Thr Gly Ala Lys Leu
            100                 105                 110

Val Lys Thr Arg Leu Glu Glu Ala Asn Leu Ile Lys Ala Ser Leu Cys
        115                 120                 125

Gly Ala Asn Leu Asn Ser Ala Asn Leu Ser Arg Cys Leu Leu Phe Gln
    130                 135                 140

Ala Asp Leu Arg Pro Ser Ser Asn Gln Arg Thr Asp Leu Gly Tyr Val
145                 150                 155                 160

Leu Leu Thr Gly Ala Asp Leu Ser Tyr Ala Asp Leu Arg Ala Ala Ser
                165                 170                 175

Leu His His Ala Asn Leu Asp Gly Ala Lys Leu Cys Arg Ala Asn Phe
            180                 185                 190

Gly Arg Thr Ile Gln Trp Gly Asn Leu Ala Ala Asp Leu Ser Gly Ala
        195                 200                 205

Ser Leu Gln Gly Ala Asp Leu Ser Tyr Ala Asn Leu Glu Ser Ala Ile
    210                 215                 220

Leu Arg Lys Ala Asn Leu Gln Gly Ala Asp Leu Thr Gly Ala Ile Leu
225                 230                 235                 240

Lys Asp Ala Glu Leu Lys Gly Ala Ile Met Pro Asp Gly Ser Ile His
                245                 250                 255

Asp


<210> SEQ ID NO 7
<211> LENGTH: 124
<212> TYPE: PRT
<213> ORGANISM: Artificial Sequence
<220> FEATURE:
<223> OTHER INFORMATION: synthetic peptide - chain A, recombinant human
      alpha lactalbumin

<400> SEQUENCE: 7

Met Lys Gln Phe Thr Lys Cys Glu Leu Ser Gln Leu Leu Lys Asp Ile
1               5                   10                  15

Asp Gly Tyr Gly Gly Ile Ala Leu Pro Glu Leu Ile Cys Thr Met Phe
            20                  25                  30

His Thr Ser Gly Tyr Asp Thr Gln Ala Ile Val Glu Asn Asn Glu Ser
        35                  40                  45

Thr Glu Tyr Gly Leu Phe Gln Ile Ser Asn Lys Leu Trp Cys Lys Ser
    50                  55                  60

Ser Gln Val Pro Gln Ser Arg Asn Ile Cys Asp Ile Ser Cys Asp Lys
65                  70                  75                  80

Phe Leu Asp Asp Asp Ile Thr Asp Asp Ile Met Cys Ala Lys Lys Ile
                85                  90                  95
```

```
Leu Asp Ile Lys Gly Ile Asp Tyr Trp Leu Ala His Lys Ala Leu Cys
            100                 105                 110

Thr Glu Lys Leu Glu Gln Trp Leu Cys Glu Lys Leu
        115                 120


<210> SEQ ID NO 8
<211> LENGTH: 133
<212> TYPE: PRT
<213> ORGANISM: Lolium perenne

<400> SEQUENCE: 8

Met Asp Glu Gln Pro Asn Thr Ile Ser Gly Ser Asn Asn Thr Val Arg
1               5                   10                  15

Ser Gly Ser Lys Asn Val Leu Ala Gly Asn Asp Asn Thr Val Ile Ser
            20                  25                  30

Gly Asp Asn Asn Ser Val Ser Gly Ser Asn Asn Thr Val Val Ser Gly
        35                  40                  45

Asn Asp Asn Thr Val Thr Gly Ser Asn His Val Val Ser Gly Thr Asn
    50                  55                  60

His Ile Val Thr Asp Asn Asn Asn Asn Val Ser Gly Asn Asp Asn Asn
65                  70                  75                  80

Val Ser Gly Ser Phe His Thr Val Ser Gly Gly His Asn Thr Val Ser
                85                  90                  95

Gly Ser Asn Asn Thr Val Ser Gly Ser Asn His Val Val Ser Gly Ser
            100                 105                 110

Asn Lys Val Val Thr Asp Ala Ala Lys Leu Ala Ala Ala Leu Glu His
        115                 120                 125

His His His His His
    130


<210> SEQ ID NO 9
<211> LENGTH: 133
<212> TYPE: PRT
<213> ORGANISM: Lolium perenne

<400> SEQUENCE: 9

Met Asp Glu Gln Pro Asn Thr Ile Ser Gly Ser Asn Asn Thr Val Arg
1               5                   10                  15

Ser Gly Ser Lys Asn Val Leu Ala Gly Asn Asp Asn Thr Val Ile Ser
            20                  25                  30

Gly Asp Asn Asn Ser Val Ser Gly Ser Asn Asn Thr Val Val Ser Gly
        35                  40                  45

Asn Asp Asn Thr Val Thr Gly Ser Asn His Val Val Ser Gly Thr Asn
    50                  55                  60

His Ile Val Thr Asp Asn Asn Asn Asn Val Ser Gly Asn Asp Asn Asn
65                  70                  75                  80

Val Ser Gly Ser Phe His Thr Val Ser Gly Gly His Asn Thr Val Ser
                85                  90                  95

Gly Ser Asn Asn Thr Val Ser Gly Ser Asn His Val Val Ser Gly Ser
            100                 105                 110

Asn Lys Val Val Thr Asp Ala Ala Lys Leu Ala Ala Ala Leu Glu His
        115                 120                 125

His His His His His
    130


<210> SEQ ID NO 10
```

-continued

<211> LENGTH: 334
<212> TYPE: PRT
<213> ORGANISM: Salmonella cholera
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid

<400> SEQUENCE: 10

```
Xaa Thr Lys Tyr Arg Leu Ser Glu Gly Pro Arg Ala Phe Thr Tyr Gln
1               5                   10                  15

Val Asp Gly Glu Lys Lys Ser Val Leu Leu Arg Gln Val Ile Ala Val
            20                  25                  30

Thr Asp Phe Asn Asp Val Lys Ala Gly Thr Ser Gly Gly Trp Val Asp
        35                  40                  45

Ala Asp Asn Val Leu Ser Gln Gln Gly Asp Cys Trp Ile Tyr Asp Glu
    50                  55                  60

Asn Ala Xaa Ala Phe Ala Gly Thr Glu Ile Thr Gly Asn Ala Arg Ile
65                  70                  75                  80

Thr Gln Pro Cys Thr Leu Tyr Asn Asn Val Arg Ile Gly Asp Asn Val
                85                  90                  95

Trp Ile Asp Arg Ala Asp Ile Ser Asp Gly Ala Arg Ile Ser Asp Asn
            100                 105                 110

Val Thr Ile Gln Ser Ser Ser Val Arg Glu Glu Cys Ala Ile Tyr Gly
        115                 120                 125

Asp Ala Arg Val Leu Asn Gln Ser Glu Ile Leu Ala Ile Gln Gly Leu
    130                 135                 140

Thr His Glu His Ala Gln Ile Leu Gln Ile Tyr Asp Arg Ala Thr Val
145                 150                 155                 160

Asn His Ser Arg Ile Val His Gln Val Gln Leu Tyr Gly Asn Ala Thr
                165                 170                 175

Ile Thr His Ala Phe Ile Glu His Arg Ala Glu Val Phe Asp Phe Ala
            180                 185                 190

Leu Ile Glu Gly Asp Lys Asp Asn Asn Val Trp Ile Cys Asp Cys Ala
        195                 200                 205

Lys Val Tyr Gly His Ala Arg Val Ile Ala Gly Thr Glu Glu Asp Ala
    210                 215                 220

Ile Pro Thr Leu Arg Tyr Ser Ser Gln Val Ala Glu His Ala Leu Ile
225                 230                 235                 240

Glu Gly Asn Cys Val Leu Lys His His Val Leu Val Gly Gly His Ala
                245                 250                 255

Glu Val Arg Gly Gly Pro Ile Leu Leu Asp Asp Arg Val Leu Ile Glu
            260                 265                 270

Gly His Ala Cys Ile Gln Gly Glu Ile Leu Ile Glu Arg Gln Val Glu
        275                 280                 285

Ile Ser Gly Arg Ala Ala Val Ile Ala Phe Asp Asp Asn Thr Ile His
    290                 295                 300

Leu Arg Gly Pro Lys Val Ile Asn Gly Glu Asp Arg Ile Thr Arg Thr
305                 310                 315                 320

Pro Leu Val Gly Ser Leu Leu Glu His His His His His His
                325                 330
```

<210> SEQ ID NO 11

```
<211> LENGTH: 334
<212> TYPE: PRT
<213> ORGANISM: Salmonella cholera
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid

<400> SEQUENCE: 11

Xaa Thr Lys Tyr Arg Leu Ser Glu Gly Pro Arg Ala Phe Thr Tyr Gln
1               5                   10                  15

Val Asp Gly Glu Lys Lys Ser Val Leu Leu Arg Gln Val Ile Ala Val
            20                  25                  30

Thr Asp Phe Asn Asp Val Lys Ala Gly Thr Ser Gly Gly Trp Val Asp
        35                  40                  45

Ala Asp Asn Val Leu Ser Gln Gln Gly Asp Cys Trp Ile Tyr Asp Glu
    50                  55                  60

Asn Ala Xaa Ala Phe Ala Gly Thr Glu Ile Thr Gly Asn Ala Arg Ile
65                  70                  75                  80

Thr Gln Pro Cys Thr Leu Tyr Asn Asn Val Arg Ile Gly Asp Asn Val
                85                  90                  95

Trp Ile Asp Arg Ala Asp Ile Ser Asp Gly Ala Arg Ile Ser Asp Asn
            100                 105                 110

Val Thr Ile Gln Ser Ser Ser Val Arg Glu Glu Cys Ala Ile Tyr Gly
        115                 120                 125

Asp Ala Arg Val Leu Asn Gln Ser Glu Ile Leu Ala Ile Gln Gly Leu
    130                 135                 140

Thr His Glu His Ala Gln Ile Leu Gln Ile Tyr Asp Arg Ala Thr Val
145                 150                 155                 160

Asn His Ser Arg Ile Val His Gln Val Gln Leu Tyr Gly Asn Ala Thr
                165                 170                 175

Ile Thr His Ala Phe Ile Glu His Arg Ala Glu Val Phe Asp Phe Ala
            180                 185                 190

Leu Ile Glu Gly Asp Lys Asp Asn Asn Val Trp Ile Cys Asp Cys Ala
        195                 200                 205

Lys Val Tyr Gly His Ala Arg Val Ile Ala Gly Thr Glu Glu Asp Ala
    210                 215                 220

Ile Pro Thr Leu Arg Tyr Ser Ser Gln Val Ala Glu His Ala Leu Ile
225                 230                 235                 240

Glu Gly Asn Cys Val Leu Lys His His Val Leu Val Gly Gly His Ala
                245                 250                 255

Glu Val Arg Gly Gly Pro Ile Leu Leu Asp Asp Arg Val Leu Ile Glu
            260                 265                 270

Gly His Ala Cys Ile Gln Gly Glu Ile Leu Ile Glu Arg Gln Val Glu
        275                 280                 285

Ile Ser Gly Arg Ala Ala Val Ile Ala Phe Asp Asp Asn Thr Ile His
    290                 295                 300

Leu Arg Gly Pro Lys Val Ile Asn Gly Glu Asp Arg Ile Thr Arg Thr
305                 310                 315                 320

Pro Leu Val Gly Ser Leu Leu Glu His His His His His His
                325                 330

<210> SEQ ID NO 12
```

<211> LENGTH: 121
<212> TYPE: PRT
<213> ORGANISM: Choristoneura fumiferana

<400> SEQUENCE: 12

Asp Gly Thr Cys Val Asn Thr Asn Ser Gln Ile Thr Ala Asn Ser Gln
1 5 10 15

Cys Val Lys Ser Thr Ala Thr Asn Cys Tyr Ile Asp Asn Ser Gln Leu
20 25 30

Val Asp Thr Ser Ile Cys Thr Arg Ser Gln Tyr Ser Asp Ala Asn Val
35 40 45

Lys Lys Ser Val Thr Thr Asp Cys Asn Ile Asp Lys Ser Gln Val Tyr
50 55 60

Leu Thr Thr Cys Thr Gly Ser Gln Tyr Asn Gly Ile Tyr Ile Arg Ser
65 70 75 80

Ser Thr Thr Thr Gly Thr Ser Ile Ser Gly Pro Gly Cys Ser Ile Ser
85 90 95

Thr Cys Thr Ile Thr Arg Gly Val Ala Thr Pro Ala Ala Ala Cys Lys
100 105 110

Ile Ser Gly Cys Ser Leu Ser Ala Met
115 120

<210> SEQ ID NO 13
<211> LENGTH: 121
<212> TYPE: PRT
<213> ORGANISM: Choristoneura fumiferana

<400> SEQUENCE: 13

Asp Gly Thr Cys Val Asn Thr Asn Ser Gln Ile Thr Ala Asn Ser Gln
1 5 10 15

Cys Val Lys Ser Thr Ala Thr Asn Cys Tyr Ile Asp Asn Ser Gln Leu
20 25 30

Val Asp Thr Ser Ile Cys Thr Arg Ser Gln Tyr Ser Asp Ala Asn Val
35 40 45

Lys Lys Ser Val Thr Thr Asp Cys Asn Ile Asp Lys Ser Gln Val Tyr
50 55 60

Leu Thr Thr Cys Thr Gly Ser Gln Tyr Asn Gly Ile Tyr Ile Arg Ser
65 70 75 80

Ser Thr Thr Thr Gly Thr Ser Ile Ser Gly Pro Gly Cys Ser Ile Ser
85 90 95

Thr Cys Thr Ile Thr Arg Gly Val Ala Thr Pro Ala Ala Ala Cys Lys
100 105 110

Ile Ser Gly Cys Ser Leu Ser Ala Met
115 120

<210> SEQ ID NO 14
<211> LENGTH: 121
<212> TYPE: PRT
<213> ORGANISM: Choristoneura fumiferana

<400> SEQUENCE: 14

Asp Gly Thr Cys Val Asn Thr Asn Ser Gln Ile Thr Ala Asn Ser Gln
1 5 10 15

Cys Val Lys Ser Thr Ala Thr Asn Cys Tyr Ile Asp Asn Ser Gln Leu
20 25 30

Val Asp Thr Ser Ile Cys Thr Arg Ser Gln Tyr Ser Asp Ala Asn Val
35 40 45

-continued

```
Lys Lys Ser Val Thr Thr Asp Cys Asn Ile Asp Lys Ser Gln Val Tyr
    50                  55                  60

Leu Thr Thr Cys Thr Gly Ser Gln Tyr Asn Gly Ile Tyr Ile Arg Ser
65                  70                  75                  80

Ser Thr Thr Thr Gly Thr Ser Ile Ser Gly Pro Gly Cys Ser Ile Ser
                85                  90                  95

Thr Cys Thr Ile Thr Arg Gly Val Ala Thr Pro Ala Ala Ala Cys Lys
            100                 105                 110

Ile Ser Gly Cys Ser Leu Ser Ala Met
        115                 120


<210> SEQ ID NO 15
<211> LENGTH: 121
<212> TYPE: PRT
<213> ORGANISM: Choristoneura fumiferana

<400> SEQUENCE: 15

Asp Gly Thr Cys Val Asn Thr Asn Ser Gln Ile Thr Ala Asn Ser Gln
1               5                   10                  15

Cys Val Lys Ser Thr Ala Thr Asn Cys Tyr Ile Asp Asn Ser Gln Leu
            20                  25                  30

Val Asp Thr Ser Ile Cys Thr Arg Ser Gln Tyr Ser Asp Ala Asn Val
        35                  40                  45

Lys Lys Ser Val Thr Thr Asp Cys Asn Ile Asp Lys Ser Gln Val Tyr
    50                  55                  60

Leu Thr Thr Cys Thr Gly Ser Gln Tyr Asn Gly Ile Tyr Ile Arg Ser
65                  70                  75                  80

Ser Thr Thr Thr Gly Thr Ser Ile Ser Gly Pro Gly Cys Ser Ile Ser
                85                  90                  95

Thr Cys Thr Ile Thr Arg Gly Val Ala Thr Pro Ala Ala Ala Cys Lys
            100                 105                 110

Ile Ser Gly Cys Ser Leu Ser Ala Met
        115                 120
```